US012029399B2

(12) United States Patent
Small et al.

(10) Patent No.: US 12,029,399 B2
(45) Date of Patent: Jul. 9, 2024

(54) MARKER DELIVERY DEVICE WITH STERILE GUIDE

(71) Applicant: Devicor Medical Products, Inc., Cincinnati, OH (US)

(72) Inventors: Andrew Small, Cincinnati, OH (US); Brennan Gallagher McCabe, Cincinnati, OH (US); Elijah Kreider, Hamilton, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 567 days.

(21) Appl. No.: 16/789,617

(22) Filed: Feb. 13, 2020

(65) Prior Publication Data

US 2020/0261067 A1 Aug. 20, 2020

Related U.S. Application Data

(60) Provisional application No. 62/806,227, filed on Feb. 15, 2019.

(51) Int. Cl.
*A61B 10/02* (2006.01)
*A61B 90/00* (2016.01)
*A61B 10/06* (2006.01)

(52) U.S. Cl.
CPC .......... *A61B 10/0266* (2013.01); *A61B 90/39* (2016.02); *A61B 2010/0208* (2013.01); *A61B 10/06* (2013.01); *A61B 2090/3908* (2016.02); *A61B 2090/3925* (2016.02)

(58) Field of Classification Search
CPC ..... A61B 10/0266; A61B 90/39; A61B 10/06; A61B 2010/0208; A61B 2090/3908; A61B 2090/3925; A61B 2090/3987
See application file for complete search history.

(56) References Cited

U.S. PATENT DOCUMENTS 3,112,747 A * 12/1963 Cowley ................ A61M 5/002 604/199
4,723,948 A * 2/1988 Clark .................... A61M 39/12 604/905
4,774,948 A 10/1988 Markham
5,526,822 A 6/1996 Burbank et al.
5,928,164 A 7/1999 Burbank et al.
6,017,316 A 1/2000 Ritchart et al.
(Continued)

FOREIGN PATENT DOCUMENTS

EP 1836955 9/2007
WO WO 2000/038579 7/2000

OTHER PUBLICATIONS

International Search Report and Written Opinion dated Jun. 17, 2020 for Application No. PCT/US2020/018029, 14 pages.

*Primary Examiner* — Rene T Towa
(74) *Attorney, Agent, or Firm* — Frost Brown Todd LLP

(57) ABSTRACT

An apparatus for delivery of a biopsy marker to a biopsy site includes a grip, a cannula, at least one biopsy marker, and a sterile guide. The cannula extends distally from the grip and includes a lumen extending at least partially therethrough. A maker exit opening is defined by the cannula and is in communication with the lumen. The at least one biopsy marker is disposed in the lumen for deployment through the marker exit opening. The sterile guide is slidable along the cannula and is configured to selectively fasten to the grip.

16 Claims, 14 Drawing Sheets

864
872
900
920
910
11
924
926
918
922
918
914
11
914
912
862
880
866
850
868
870

(56) References Cited

U.S. PATENT DOCUMENTS 6,086,544 A 4/2000 Hibner et al.
6,083,524 A 7/2000 Sawhney et al.
6,162,187 A 12/2000 Buzzard et al.
6,270,464 B1 8/2001 Fulton, III et al.
6,356,782 B1 3/2002 Sirimanne et al.
6,432,065 B1 8/2002 Burdorff et al.
6,517,522 B1 * 2/2003 Bell .................. A61M 25/0637 604/165.02
6,605,294 B2 8/2003 Sawhney et al.
6,626,849 B2 9/2003 Huitema et al.
6,752,768 B2 6/2004 Burdorff et al.
7,442,171 B2 10/2008 Stephens et al.
7,648,466 B2 1/2010 Stephens et al.
7,837,632 B2 11/2010 Stephens et al.
7,854,706 B2 12/2010 Hibner
7,914,464 B2 3/2011 Burdorff et al.
7,938,786 B2 5/2011 Ritchie et al.
8,083,687 B2 12/2011 Parihar
8,118,755 B2 2/2012 Hibner et al.
8,206,316 B2 6/2012 Hibner et al.
8,241,226 B2 8/2012 Hibner et al.
8,454,531 B2 6/2013 Speeg et al.
8,600,481 B2 12/2013 Sirimanni et al.
8,622,924 B2 1/2014 Speeg et al.
8,702,623 B2 4/2014 Parihar et al.
8,764,680 B2 7/2014 Rhad et al.
8,801,742 B2 8/2014 Rhad et al.
8,858,465 B2 10/2014 Fiebig
8,938,285 B2 1/2015 Fiebig et al.
8,939,910 B2 1/2015 Fisher
9,095,326 B2 8/2015 Ritchie et al.
9,326,755 B2 5/2016 Fiebig et al.
9,345,457 B2 5/2016 Speeg et al.
9,788,819 B2 10/2017 Householder et al.
9,877,706 B2 1/2018 Speeg et al.
9,999,406 B2 6/2018 Hibner et al.
2006/0074345 A1 4/2006 Hibner
2009/0131821 A1 5/2009 Speeg et al.
2009/0209853 A1 8/2009 Parihar et al.
2009/0209854 A1 * 8/2009 Parihar .................. A61B 90/39 600/431
2010/0152610 A1 6/2010 Parihar et al.
2010/0160819 A1 6/2010 Parihar et al.
2011/0218433 A1 * 9/2011 Speeg .................... A61B 10/02 600/432
2013/0237912 A1 9/2013 Speeg
2013/0324882 A1 12/2013 Mescher
2015/0217092 A1 * 8/2015 Kokate ............. A61M 25/1038 604/103.05

* cited by examiner 870
866
868
880
850
862
900
920
910
918
11
924
926
922
918
914
912
914
864
872

MARKER DELIVERY DEVICE WITH STERILE GUIDE

PRIORITY

This application claims priority to U.S. Provisional Patent App. 62/806,227 entitled "Marker Delivery Device with Sterile Guide," filed on Feb. 15, 2019, the disclosure of which is incorporated by reference herein.

BACKGROUND

A number of patients will have breast biopsies because of irregular mammograms and palpable abnormalities. Biopsies can include surgical excisional biopsies and stereotactic and ultrasound guided needle breast biopsies. In the case of image directed biopsy, the radiologist or other physician may take a small sample of the irregular tissue for laboratory analysis. If the biopsy proves to be malignant, additional surgery (e.g., a lumpectomy or a mastectomy) may be required. In the case of needle biopsies, the patient may return to the radiologist a day or more later, and the biopsy site (the site of the lesion) may need to be relocated in preparation for the surgery. An imaging system, such as ultrasound, magnetic resonance imaging (MRI) or x-ray may be used to locate the biopsy site. In order to assist the relocation of the biopsy site, a marker may be placed at the time of the biopsy.

The use of markers used after breast biopsies to mark the location where the biopsied tissue was removed is described in the following U.S. Pat. No.: 6,083,524, "Polymerizable biodegradable polymers including carbonate or dioxanone linkages," issued Jul. 4, 2000; U.S. Pat. No. 6,162,241, "Hemostatic tissue sealants," issued Dec. 4, 2000; U.S. Pat. No. 6,270,464, "Biopsy localization method and device," issued Aug. 7, 2001; U.S. Pat. No. 6,356,782, "Subcutaneous cavity marking device and method," issued Mar. 12, 2002; U.S. Pat. No. 6,605,294, "Methods of using in situ hydration of hydrogel articles for sealing or augmentation of tissue or vessels," issued Aug. 12, 2003; U.S. Pat. No. 8,600,481, "Subcutaneous cavity marking device," issued Dec. 3, 2013 and U.S. Pat. No. 8,939,910, "Method for enhancing ultrasound visibility of hyperechoic materials", issued Jan. 27, 2015. All of these US Patents are incorporated by reference in their entirety.

In some contexts, a marker biopsy site marker is used to identify a biopsy site after a biopsy procedure. In some examples such biopsy site markers can be deployed at a biopsy site through a biopsy needle using a side-deploy marker delivery device. In this configuration, the marker delivery device includes a side aperture that corresponds to the side aperture of the biopsy needle. Thus, in such configurations the marker delivery device includes a cannula that is inserted through a biopsy needle. Because of the length of the biopsy needle, the cannula of the marker delivery device may be relatively long and flexible. This can in turn make manipulation of the cannula while maintaining sterility difficult. Accordingly, in some contexts, it may be desirable to include various features to aid with manipulation of the cannula of the marker delivery device while maintaining sterility of the cannula. While several systems and methods have been made and used for marking a biopsy site, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1C:
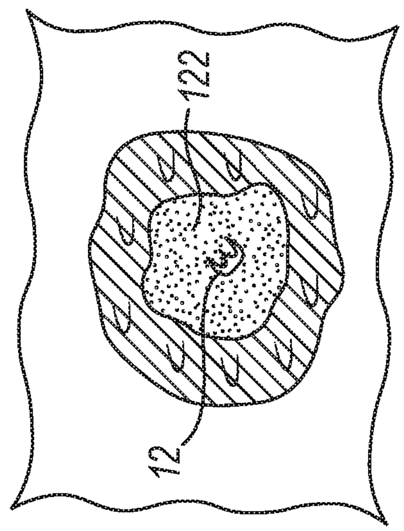
FIGS. 1A, 1B, and 1C show exemplary aspects of placement of a biopsy site marker, in accordance with aspects of the present disclosure.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It may be beneficial to be able to mark the location or margins of a lesion, whether temporarily or permanently, prior to or immediately after removing or sampling it. Marking prior to removal may help to ensure that the entire lesion is excised, if desired. Alternatively, if the lesion were inadvertently removed in its entirety, marking the biopsy site immediately after the procedure would enable reestablishment of its location for future identification.

Once a marker is positioned at a biopsy site, it may be desirable for the marker to remain visible under ultrasound. It may also be desirable to make the marker readily identifiable relative to other structural features of a patient. For instance, it may be desirable for the marker to be distinguishable under ultrasound visualization from microcalcifications to avoid inadvertently characterizing the marker as a microcalcification during subsequent ultrasonic examinations. Generally, microcalcifications are used in the field to identify suspicious lesions or masses. Thus, it is generally desirable for the ultrasound view to be distinguishable as a marker and not inadvertently identified as a new mass.

I. Exemplary Marker

Figure 1B:
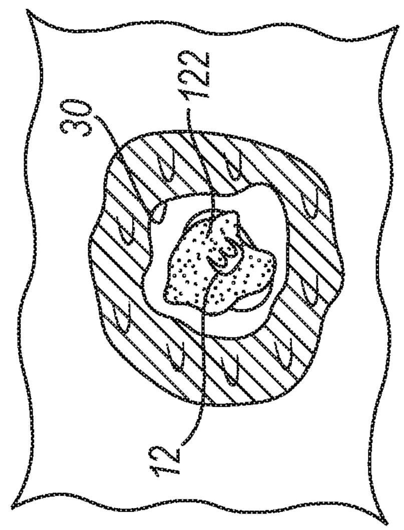
Figure 1A:
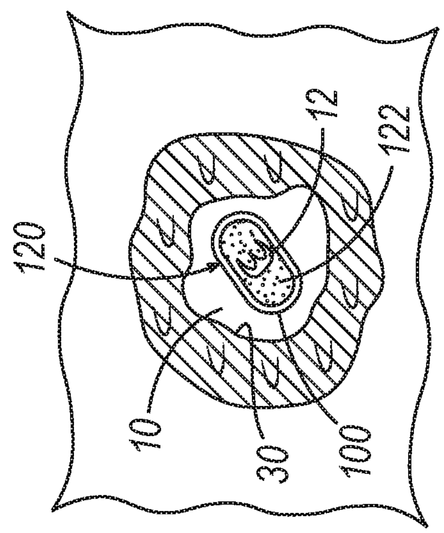

Aspects presented herein relate to devices and procedures for manufacturing a marker for percutaneously marking a biopsy cavity (10) having surrounding tissue (30), as shown in FIGS. 1A-1C. For instance, as seen in FIG. 1A, a marker (100) may be initially placed in the biopsy cavity (10) to facilitate relocation of the biopsy site. Marker (100) may comprise a carrier (120) and a marker element (12). Carrier (120) generally includes a bioabsorbable marker material (122). Thus, carrier (120) is generally configured for absorption into a patient after placement of marker (100) within the biopsy cavity (10). In some examples, carrier (120) can include a plurality of microbubbles to enhance visualization of carrier (120) under ultrasound. As will be described in greater detail below, marker material (122) is generally bioabsorbable such that marker material (122) may be generally absorbed into the patient's tissue over time. In the present example, marker material (122) comprises a hydrogel that is initially in a dehydrated state. Although a hydrogel is used in the present example, it should be understood that in other examples marker material (122) may comprise other known bioabsorbable materials In the present example, marker (100) further includes a marker element (12) that is generally not bioabsorbable. Marker element (12) may comprise a radiopaque or echogenic marker embedded within the bioabsorbable marker material (122) of carrier (120). For instance, marker element (12) may comprise metal, hard plastic, or other radiopaque or hyperechoic materials known to those of ordinary skill in the art in view of the teachings herein. In other examples, marker (100) may be formed without a marker element (12). In still other examples, marker (100) may be formed with only marker element (12) such that carrier (120) is omitted and marker element (12) is in a "bare" form. In other words, in some examples marker (100) is formed of only carrier (120) as a bare clip.

Marker material (122) is generally expandable once disposed within a patient at a biopsy site. As shown in FIGS. 1B and 1C, the initially dehydrated marker material (122) may absorb fluid from the surrounding tissue (30) into which it is inserted. In response to this absorption of fluid, maker material (122) may swell, thereby permitting carrier (120) to fill a cavity formed at a biopsy site by removal of tissue samples during a biopsy procedure. Biodegradable materials may be particularly suitable in applications where it is desired that natural tissue growth be permitted to completely or partially replace the implanted material over time. Accordingly, biocompatibility is ensured and the natural mechanical parameters of the tissue are substantially restored to those of the pre-damaged condition.

Marker (100) may be inserted into the body either surgically via an opening in the body cavity (30), or through a minimally invasive procedure using such devices as a catheter, introducer or similar type insertion device. Marker (100) may be delivered immediately after removal of the tissue specimen using the same device used to remove the tissue specimen itself. Follow-up noninvasive detection techniques, such as x-ray mammography or ultrasound may then be used by the physician to identify, locate, and monitor the biopsy cavity site over a period of time via marker (100).

Marker (100) of the present example is large enough to be readily visible to a clinician under x-ray or ultrasonic viewing, for example; yet small enough to be able to be percutaneously deployed into the biopsy cavity and to not cause any difficulties with the patient. Although examples are described in connection with treatment and diagnosis of breast tissue, aspects presented herein may be used for markers in any internal, tissue, e.g., in breast tissue, lung tissue, prostate tissue, lymph gland tissue, etc.

The hydration of the marker material (122) of carrier (120) by the natural moisture of the tissue surrounding it causes expansion of the polymer and thus minimizes the risk of migration. The growing hydrogel based marker material (122) centers marker (100) in the biopsy cavity as it grows. As the hydrogel expands, naturally-present moisture from the surrounding tissue, the hydration enables increasing sound through transmission, appears more and more hypoechoic and is easy to visualize on follow up ultrasound studies.

The hydrated hydrogel marker material (122) of carrier (120) may also be used to frame permanent marker (12). The hypoechoic nature of the hydrated marker material (122) enables ultrasound visibility of the permanent marker (12) within the hydrogel hydrated marker material (122) because the permanent marker (12) is outlined as a specular reflector within a hypoechoic hydrated marker having a water-like nonreflective substrate.

II. Exemplary Marker Delivery Device

Figure 2:
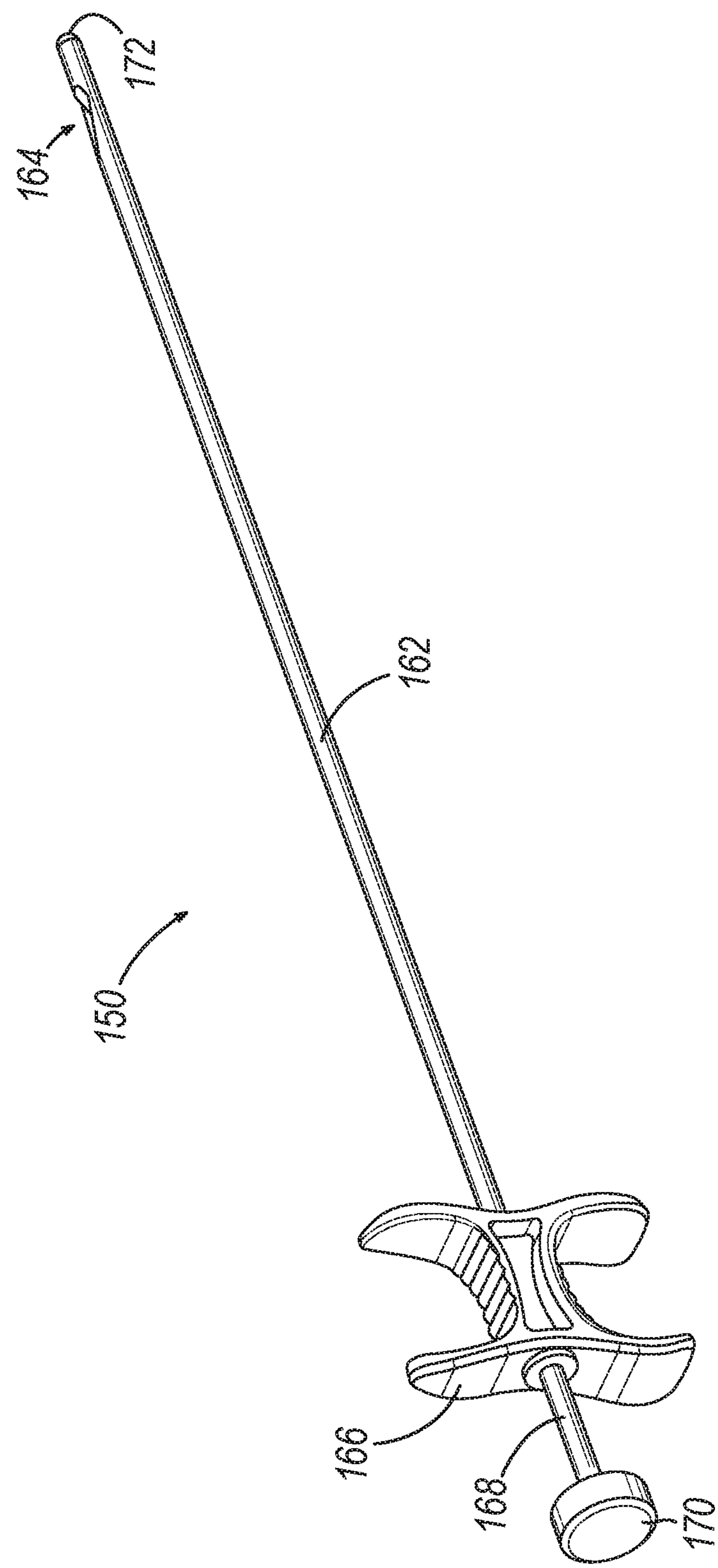
FIG. 2 depicts a perspective view of an exemplary marker delivery device.
Figure 3:
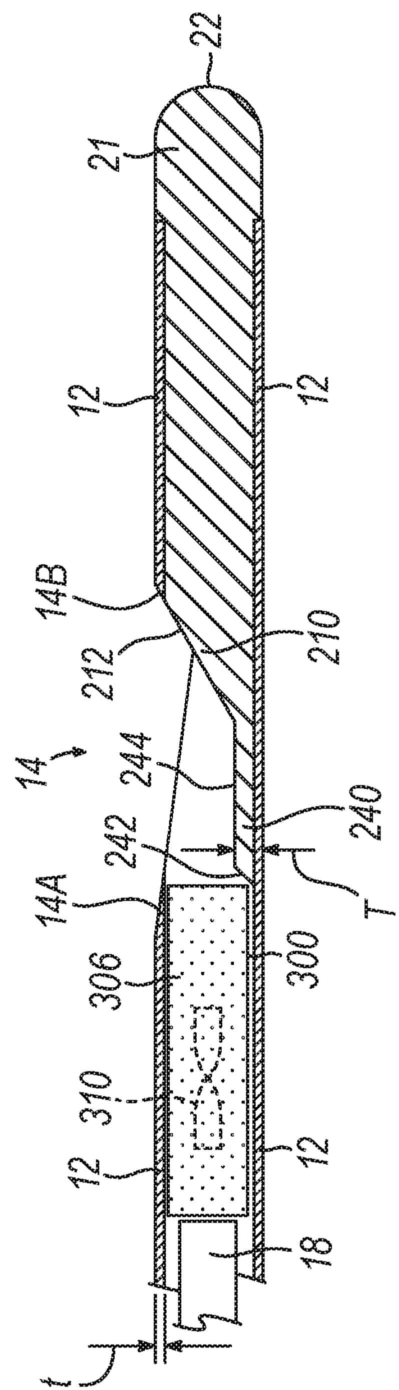
FIG. 3 depicts a side cross-sectional view of the marker delivery device of FIG. 2.

In some examples it may be desirable to deploy marker (100) described above within the body cavity (30) using certain marker delivery devices. For instance, FIGS. 2 and 3 show an exemplary marker delivery device (150) which includes an elongate outer cannula (162) having a marker exit, such as side opening (164) formed adjacent to, but spaced proximally from, the distal end of the cannula (162). It should be understood that the term "cannula" used herein refers a hollow tube or sheath.

A grip (166) can be provided at the proximal end of cannula (162). A push rod (168) can be provided, with push rod (168) extending coaxially in cannula (162) such that push rod (168) is configured to translate within cannula (162) to displace one or more markers through side opening (164) (see FIG. 3). Rod (168) may have sufficient rigidity in compression to push a marker from an internal lumen (165) of cannula (162) out through opening (164), yet be relatively flexible in bending. A plunger (170) is coupled at the proximal end of rod (168) for forcing rod (168) distally in cannula (162) to deploy a marker out of cannula (162).

A user may grasp grip (166) with two fingers, and may push on plunger (170) using the thumb on the same hand, so that marker delivery device (160) is operated by a user's single hand. A spring (not shown) or other feature may be provided about rod (168) to bias rod (168) proximally relative to grip (166) and cannula (162).

FIG. 3 shows a cross-sectional view of a distal portion of the marker delivery device (160). As can be seen, a biopsy marker (300) similar to marker (100) described above is disposed within internal lumen (165) of cannula (162). In the present example, marker (300) comprise a biodegradable or otherwise resorbable marker material (306), such as a generally cylindrically shaped body of collagen, hydrogel, or etc., and a metallic, generally radiopaque permanent marker or marker element (310) (shown in phantom) disposed within or otherwise carried by marker material (306).

Cannula (162) may be formed of any suitable metallic or non-metallic material. In some versions, cannula (162) is formed of a thin walled hollow tube formed of a suitable medical grade plastic or polymer. One suitable material is a thermoplastic elastomer, such as Polyether block amide (PEBA), such as is known under the tradename PEBAX. Cannula (162) may be formed of PEBAX, and may be substantially transparent to visible light and X-ray.

Side opening (164) may be formed by cutting away a portion of the wall of cannula (162). Side opening (164) communicates with an internal lumen (165) of cannula (162). Side opening (164) may extend axially (in a direction parallel to the axis of lumen (165)) from a proximal opening end (164A) to a distal opening end (164B), as illustrated in FIG. 3.

In the present example, distal tip (172) extends from the distal end of cannula (162) and is rounded as shown in FIG. 3. Referring to FIG. 3, the distal end of cannula (162) is closed by a unitary endpiece (171), with a portion of endpiece (171) extending into internal lumen (165) of cannula (162). Endpiece (171) may be a molded or cast component. Endpiece (171) comprises a tip (172), a ramp (210) having a ramp surface (212), and a marker engaging element (240). Ramp surface (212) aids in directing marker (300) from internal lumen (165) through side opening (164). Marker engaging element (240) helps to retain marker (300) in internal lumen (165) until the user intends to deploy marker (300).

Marker engaging element (240) is disposed within internal lumen (165), and at least a portion of marker engaging element (240) is disposed distally of proximal end (164A) of side opening (164). Marker engaging element (240) extends along a portion of the floor of cannula (162) under opening (164) such that marker engaging element (240) is positioned to reinforce the portion of cannula (162) in which opening (164) is formed. For instance, by positioning marker engaging element (240) underneath opening (164), as shown in FIG. 3, element (240) helps to stiffen cannula (162) in the region where wall of cannula (162) is cut to form opening (164). As shown in FIG. 3, marker engaging element (240) extends from the proximal most portion of ramp surface (212), and does not extend proximally of side opening (164), though in other embodiments, a portion of element (240) may extend proximally of opening (164).

As shown in FIG. 3, marker engaging element (240) is in the form of a step having a generally uniform thickness (T) along element's (240) axial length, except that element (240) has a tapered proximal end (242). Tapered proximal end (242) forms an included angle with the longitudinal axis of lumen (165) (included angle with a horizontal line in FIG. 3) of about 45 degrees, while ramp surface (212) forms an included angle with the longitudinal axis of about 30 degrees. Of course, any number of other suitable angles may be used.

As shown in FIG. 3, an upwardly facing surface (244) (surface facing opening (164)) of marker engaging element (240) extends distally to contact ramp surface (212), so that there is not a space or gap between surface (244) and ramp surface (212). Such an arrangement is advantageous to reduce the possibility that marker (300), upon moving past marker engaging element (240), may become lodged between marker engagement element (240) and ramp (212). In some versions, marker engaging element (240), ramp (210), and/or tip (172) are formed of, or include, a material that is relatively more radiopaque than the wall of cannula (162). For instance, where element (240), ramp (210), and tip (172) are formed as an integral endpiece (171), endpiece (171) may include a radiopaque additive, such as barium sulfate. For instance, endpiece (171) may be a component molded of PEBAX, with about 20 percent by weight barium sulfate added to the molten PEBAX mold composition. The relatively more radiopaque marker engaging element (240), ramp (210), and tip (172) may be useful in distinguishing the position of those components using radiographic imaging. Also, where ramp (210) and/or step of engaging element (240) are positioned in association with opening (164), the addition of a radiopaque material can help identify the position of opening (164), and the position of marker (300) relative to opening (164) before, during, or after deployment of marker (300).

Figure 4:
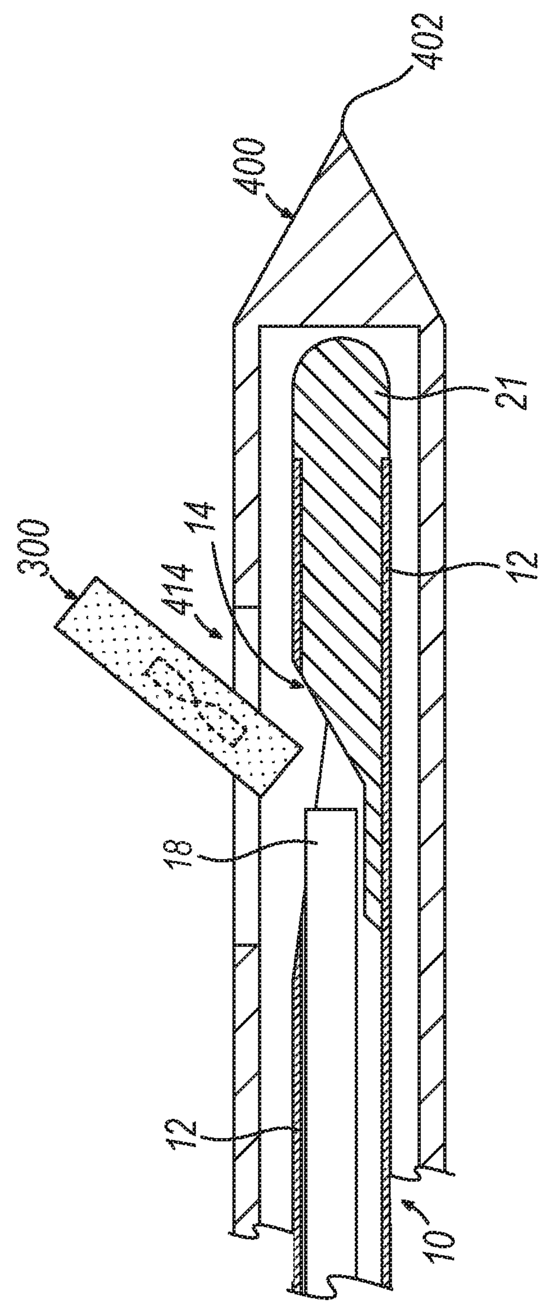
FIG. 4 depicts a cross-sectional view of a marker being deployed from the distal portion of the marker delivery device of FIG. 1 and through a lateral aperture in a biopsy needle to mark a biopsy site.

Referring to FIG. 4, marker delivery device (160) is used to deploy a marker (300) to mark a biopsy location within a patient. In FIG. 4, a cannular biopsy needle (400) is shown having a closed distal end with piercing tip (402) and a lateral tissue receiving aperture (414). Marker delivery device (160) is introduced to a biopsy site through biopsy needle (400), which may be the same needle (400) used to collect a tissue sample from the biopsy site. Biopsy needle (400) may be of the type used with single insertion, multiple sample vacuum assisted biopsy devices. Several such biopsy devices are disclosed in the various patents and patent applications that have been referred to and incorporated by reference herein, though other biopsy devices may be used.

FIG. 4 shows the distal end of marker delivery device (160) disposed within needle (400). Needle (400) may be positioned in tissue, and a biopsy sample may be obtained through lateral aperture (414), thereby providing a biopsy cavity adjacent lateral aperture (414). Then, after the tissue sample has been obtained and transferred proximally through needle (400), and without removing needle (400) from the patient's tissue, marker delivery device (160) is inserted into a proximal opening in needle (400). In FIG. 4, needle (400) and marker delivery device (160) are positioned such that opening (164) of cannula (162) and lateral aperture (414) of needle (400) are substantially aligned axially and circumferentially. Then, with marker delivery device (160) and needle (400) so positioned at the biopsy site, push rod (168) is advanced to deploy marker (300) up ramp surface (212), through opening (164), and then through lateral aperture (414), into the biopsy cavity.

III. Exemplary Marker Delivery Device with Sterile Guide

In some examples it may be desirable to retain the sterility of certain portions of a marker delivery device similar to marker delivery device (150) described above. For instance, a marker delivery device can generally be supplied to an operator in sterile packaging such that the entire marker delivery device is in a sterile condition prior to use. During use, certain components may contact a patient. Thus, it may be desirable to maintain sterility of those components. In particular, as described above, a cannula similar to cannula (162) can be inserted into a biopsy needle, targeting device, introducer, or other component or assembly disposed within a patient. Because of this, the cannula may at some point contact the patient during a marking procedure. Thus, it may be desirable to use methods and components along with the cannula to avoid disrupting the sterility thereof.

While it is desirable to maintain sterility of the cannula, it may also be desirable to provide a means for readily manipulating the cannula. For instance, the cannula can in some circumstances be relatively small and diameter and flexible. This configuration can make the cannula challenging to manipulate. Challenges can be compounded when the cannula is manipulated into small spaces such as the proximal end of a needle, tissue sample holder, introducer or other conduits or passageways. Thus, it is desirable to both maintain the sterility of the cannula while also permitting ease of manipulation. Although several specific features that satisfy these conditions are described herein, it should be understood that various alternative features or combinations of features can be used without departing from the general concepts described herein.

Figure 5:
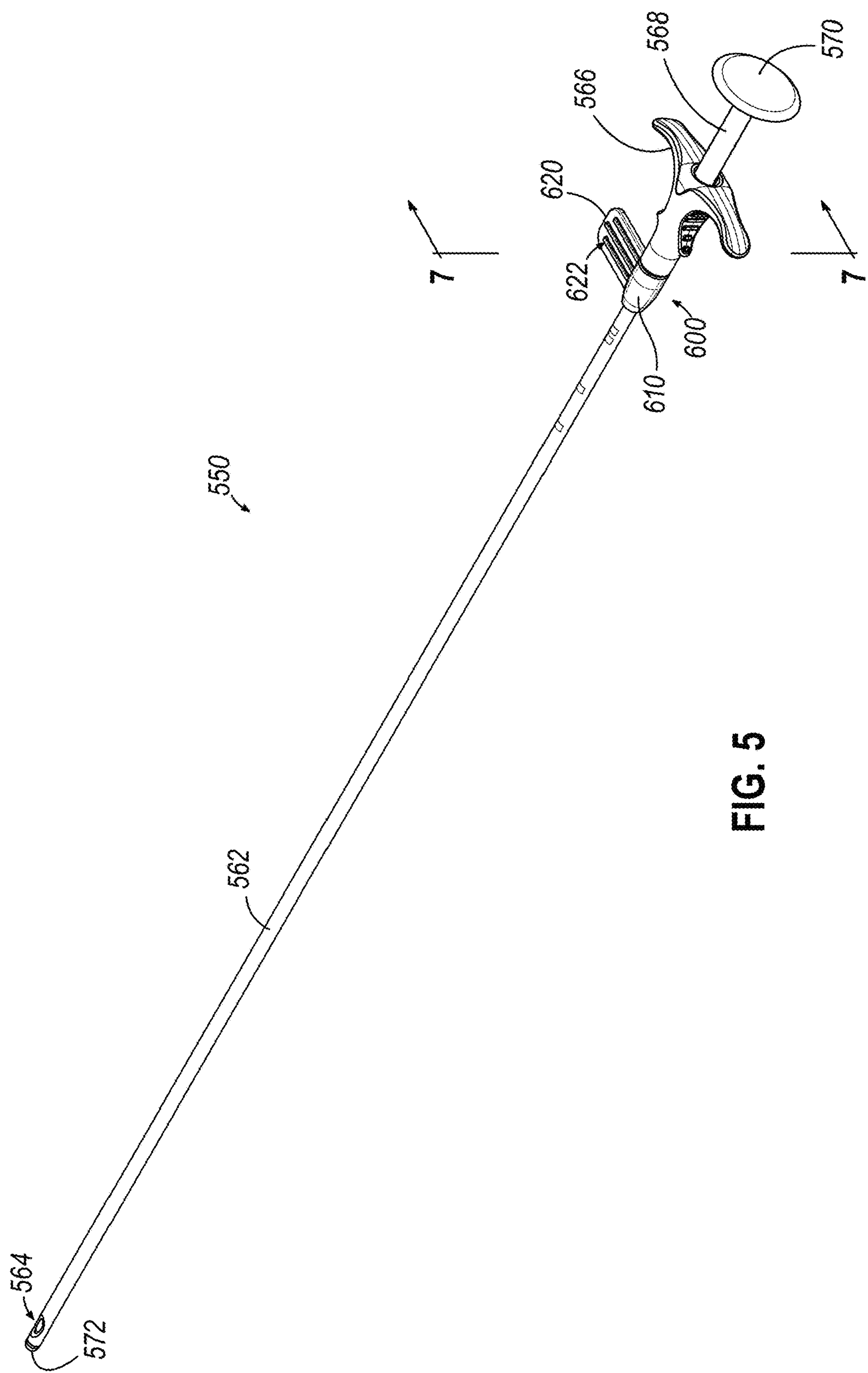
FIG. 5 depicts a perspective view of another exemplary marker delivery device.

FIG. 5 depicts a marker delivery device (550) that is substantially similar to marker delivery device (150) described above. For instance, like marker delivery device (150), marker delivery device (550) of the present example includes an elongate outer cannula (562) having a side opening or marker exit (564). Outer cannula (562) includes a distal tip (572) and is generally sized to slidably fit within a cutter or needle of a biopsy device (700), as will be described in greater detail below. Similarly, the length of cannula (562) is generally sized to correspond to the length of a corresponding cutter or needle. It should be understood that in some examples the particular length of cannula (562) can be greater than the length of a cutter or needle. For instance, in some examples the proximal end of a cutter or needle can be coupled to a tissue sample holder or other tissue collection device. In such examples, the length of cannula (562) can have a length suitable to extend through both needle/cutter and various tissue collection devices.

Like with marker delivery device (150), marker delivery device (550) of the present example includes a grip (566) at the proximal end of cannula (562). Similarly, a push rod (568) can be provided, with push rod (568) extending coaxially in cannula (562) and extending proximally from grip (566). Like push rod (168) described above, push rod (568) of the present example is configured to translate within cannula (562) to displace one or more markers through side opening (564). Push rod (568) generally can have sufficient rigidity in compression to push a marker from an internal lumen (not shown) of cannula (562) out through opening (564), yet be relatively flexible in bending. A plunger (570) is coupled at the proximal end of push rod (568) for forcing push rod (568) distally in cannula (562) to deploy a marker out of cannula (562).

Like with grip (166) described above, an operator can grasp grip (566) with two fingers, and push on plunger (570) using the thumb on the same hand, so that marker delivery device (160) is operated by a single hand. A spring (not shown) or other resilient feature may be provided about push rod (568) to bias push rod (568) proximally relative to grip (566) and cannula (562).

Unlike marker delivery device (150) described above, marker delivery device (550) of the present example further includes a sterile guide (600). It should be understood that the term "sterile" used in connection with "guide" herein refers to how the sterile guide (600) is used to preserve one or more components of a marker delivery device such as cannula (562). In other words, the term "sterile guide" is not intended to imply that any component of sterile guide (600) is sterile or should remain sterile. Instead, as will be described in greater detail below, various components of sterile guide (600) are configured for gasping directly by an operator to avoid grasping other components of a marker delivery device such as cannula (562).

Figure 6:
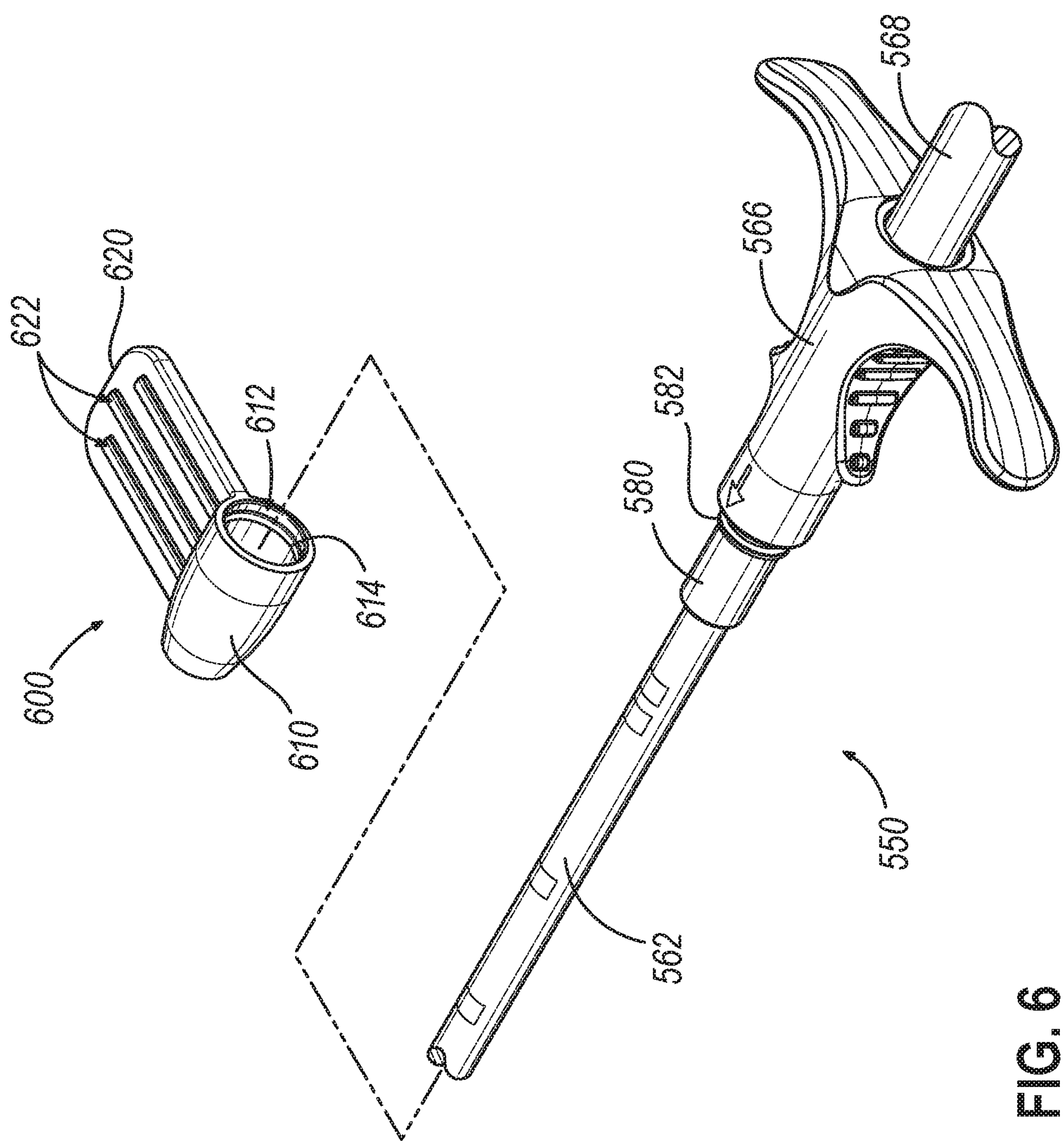
FIG. 6 depicts a detailed partially exploded perspective view of the marker delivery device of FIG. 5.

As best seen in FIG. 6, sterile guide (600) includes a body (610) with a grasping element or grip feature (620) extending therefrom. Body (610) is generally configured to receive cannula (562). In particular, body (610) defines a bore (612) extending through a central axis of body (610). Bore (612) is generally sized to receive cannula (562). As will be described in greater detail below, the inner diameter of bore (612) is slightly oversized relative to the outer diameter of cannula (562) such that body (610) is axially slidable along the length of cannula (562). In some examples, bore (612) can be configured to have a slight interference fit with cannula (562) to permit some sliding of body (610) along the length of cannula (562) while providing at least some resistance to sliding. Such a configuration can permit body (610) to be placed at a selected position and remain at said position until body (610) is moved to another position. In some examples, this interference fit can be further facilitated by body (610) being constructed of a flexible material such as elastomer. In this configuration, body (610) can act as a resilient stopper to maintain a position on cannula (562) but still slide when a force is applied by an operator.

Grip feature (610) is generally configured as an elongate wing extending from one side of body (610). Grip feature (610) is generally sized for grasping by a user and includes a plurality of ribs (622) to promote gripping. It should be understood that grip feature (610) can take on a variety of forms provided grip feature (610) provides a suitable means to grip body (610). For instance, in other examples, grip feature (610) can include multiple wings extending from opposing sides of body (610). In addition, or in the alternative, grip feature (610) or features can also be curved or rounded. Of course, various alternative configurations for grip feature (610) will be apparent to those of ordinary skill in the art in view of the teachings herein.

Sterile guide (600) is generally configured to couple to grip (566) of marker delivery device (550). In particular, as best seen in FIG. 6, marker delivery device (550) includes a retainer (580) extending distally from grip (566). Retainer (580) is generally cylindrical in shape and is configured to fit within bore (612) of sterile guide (600).

Figure 7:
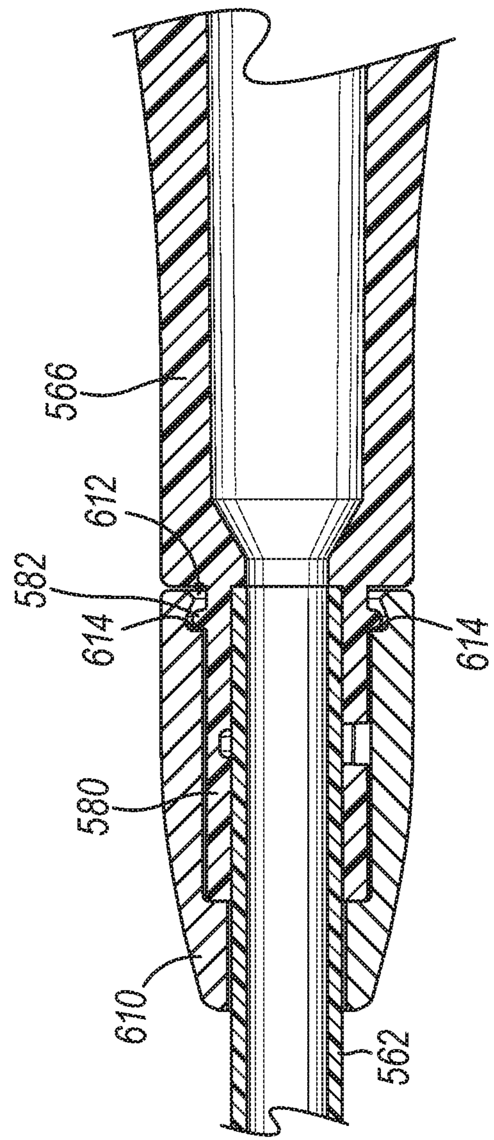
FIG. 7 depicts a side cross-sectional view of the marker delivery device of FIG. 5, the cross-section taken along line 7-7 of FIG. 5.

To facilitate fastening of sterile cover to retainer (580), retainer (580) includes a circular rib (582) extending from the outer surface of the cylindrical shape of retainer (580). Correspondingly, the interior of bore (612) includes one or more feature to receive rib (582) and fasten thereto. In particular, as best seen in FIG. 7, bore (612) includes a counterbore face (614) extending inwardly into bore (612). Counterbore face (614) is generally configured to abut the distal face of rib (582). Proximally of counterbore face (614), body (610) tapers inwardly to provide at least a partial interference fit with rib (582). It should be understood that in the present example, body (610) can be formed of a generally flexible material to facilitate flexion of body (610) to increase the diameter of bore (612) as body (610) is pulled from retainer (580). In addition, or in the alternative, in some examples rib (582) includes a resilient or flexible material to likewise flex as body (610) is pulled from retainer.

In some examples, rib (582) or body (610) can be configured to provide feedback when coupling. For instance, rib (582) or body (610) may be configured to provide tactile feedback during coupling. In addition, or in alternative, rib (582) or body (610) may be configured to provide an audible snap or crack during coupling to provide an indication that sterile guide (600) is secured to retainer (580).

Figure 8:
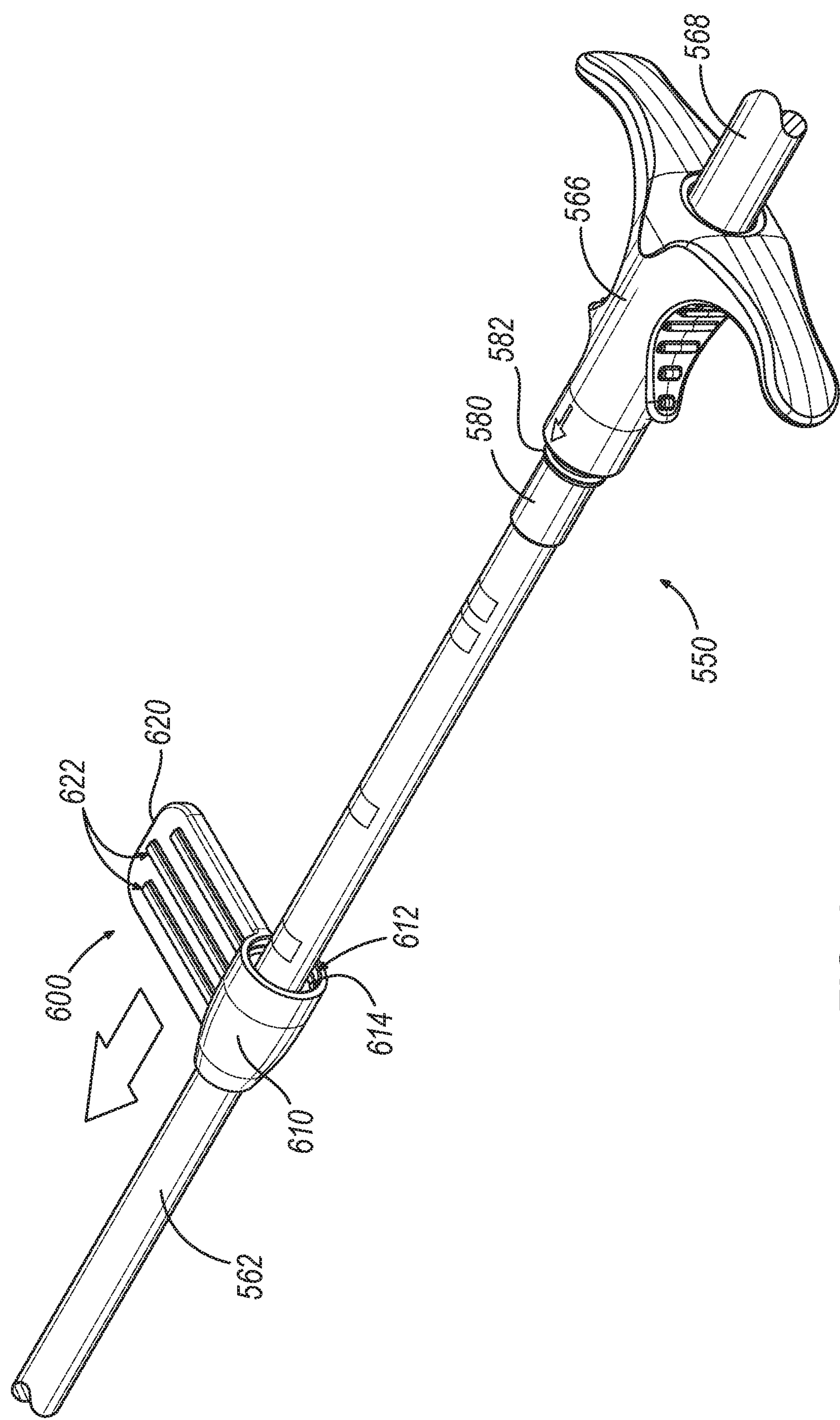
FIG. 8 depicts detailed perspective view of the marker delivery device of FIG. 5, with a sterile guide being moved distally.
Figure 9:
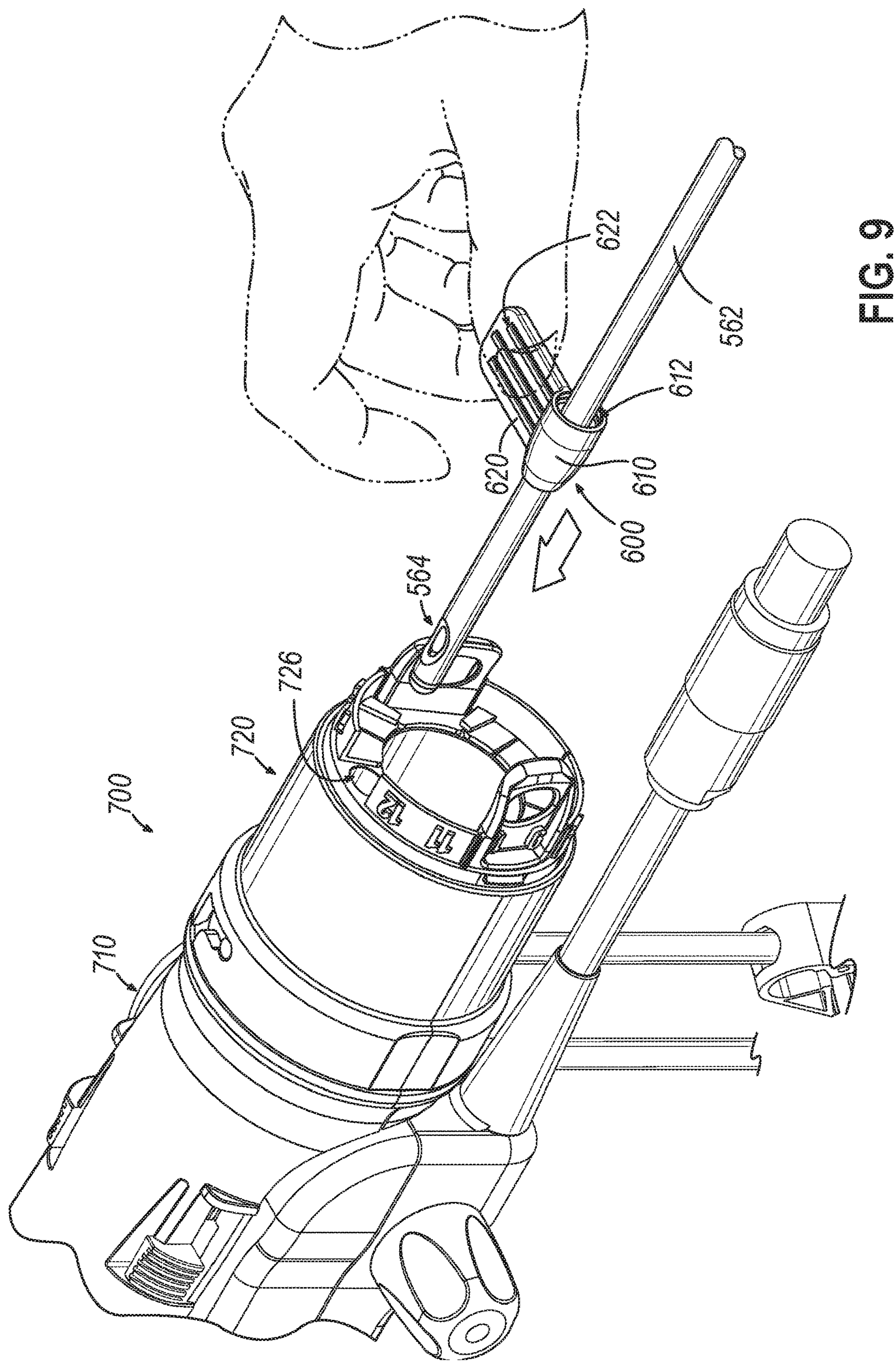
FIG. 9 depicts a detailed perspective view of the marker delivery device of FIG. 5 being inserted into an exemplary biopsy device.

FIGS. 8 and 9 show an exemplary use of sterile guide (600). As can be seen in FIG. 9, sterile guide (600) is initially pulled distally from retainer (580) of marker delivery device (550). This pulling motion releases sterile guide (600) from retainer (580) such that sterile guide (600) is free to slide axially down the length of cannula (562). At this stage, marker delivery device (550) can be pulled from associated packaging or otherwise be manipulated around a procedure room by gasping both grip (566) and sterile guide (600) using grip feature (620). Thus, sterile guide (600) is generally placed towards distal tip (572) of cannula (562), but can be placed in any other suitable position along the length of cannula (562).

Once sterile guide (600) is positioned as desired, an operator can use sterile guide (600) to manipulate cannula (562) into a biopsy device, biopsy needle, targeting set, introducer, or other components associated with a patient. One merely exemplary example of manipulation is show in FIG. 9. As can be seen, sterile guide (600) is used to manipulate distal tip (572) of cannula (562) into a marking port (726) of a tissue sample holder (720) that is attached to a proximal end of a biopsy probe (710) of a biopsy device (700). In particular, an operator can grasp grip feature (620) to manipulate cannula (562) without physically touching cannula (562). Due to the positioning of sterile guide (600) proximate the distal end of cannula (562), movement of distal tip (572) is easily controlled to position distal tip (572) into port (726). It should be understood that in some examples, biopsy device (700) can be constructed in accordance with at least some of the teachings of U.S. Pat. No. 9,877,706, entitled "Biopsy Device," issued on Jan. 30, 2018, the disclosure of which is incorporated by reference herein.

Although not shown, it should be understood that tissue sample holder (720) of the present example is rotatable to align port (726) with a cutter of biopsy device (700). The cutter is disposed within a needle similar to needle (400) described above that extends distally from probe (710). Thus, the cutter can act as a conduit between port (726) and the needle so that cannula (562) can be used to deploy marker (100) through side opening (564). Although marker delivery device (550) and sterile guide (600) of the present example are shown as being used in connection with biopsy device (700), it should be understood that in other examples the combination of marker delivery device (550) and sterile guide (600) can be used with a variety of other biopsy devices or other medical instruments. For instance, in some examples cannula (562) can be inserted directly into a cutter under the direction of sterile guide (600). In other examples, cannula (562) can be inserted using sterile guide (600) through a basket-style tissue sample holder constructed in accordance with the teachings of U.S. Pat. No. 9,999,406, the disclosure of which is incorporated by reference herein. In still other examples, cannula (562) can be inserted using sterile guide (600) through an introducer constructed in accordance with the teachings of U.S. Pat. No. 9,788,819, the disclosure of which is incorporated by reference herein. In yet other examples, the combination of marker delivery device (550) and sterile guide (600) can be used with various alternative devices as will be apparent to those of ordinary skill in the art in view of the teachings herein.

Once cannula (562) is inserted into port (726) or any other suitable component, sterile guide (600) can be slid proximally along cannula (562) back to retainer (580). Sterile guide (600) can then be re-coupled to retainer (580) for storage while marking is performed. After marking, sterile guide (600) can then be again de-coupled from retainer (580) to provide assistance to an operator with removal of cannula (562) from port (726) or any other suitable component. After the procedure is complete, marker delivery device (550) and sterile guide (600) can together be disposed of.

IV. Exemplary Marker Delivery Device with Alternative Sterile Guide

Figure 10:
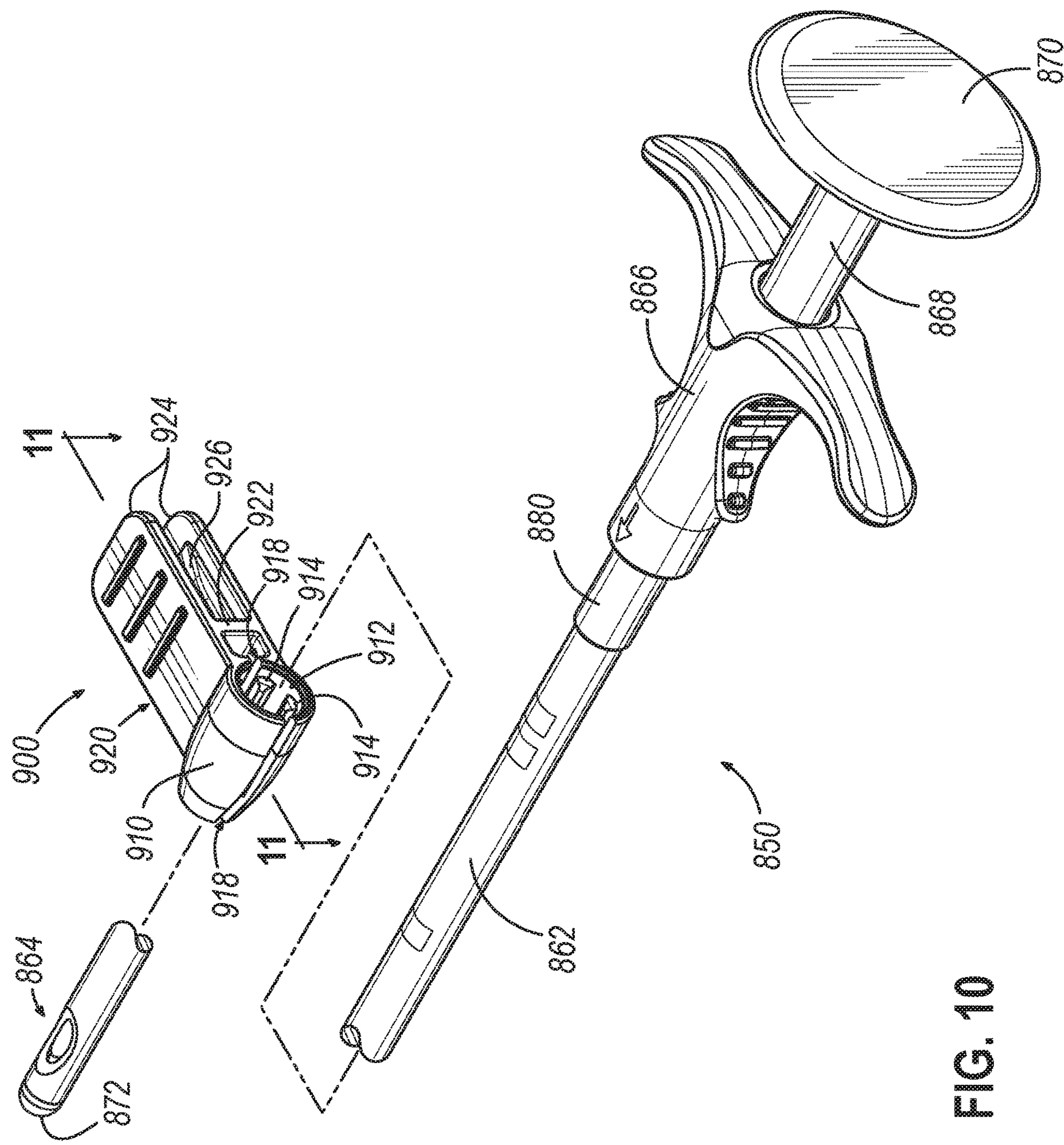
FIG. 10 depicts a detailed partially exploded perspective view of another exemplary marker delivery device.
Figure 11:
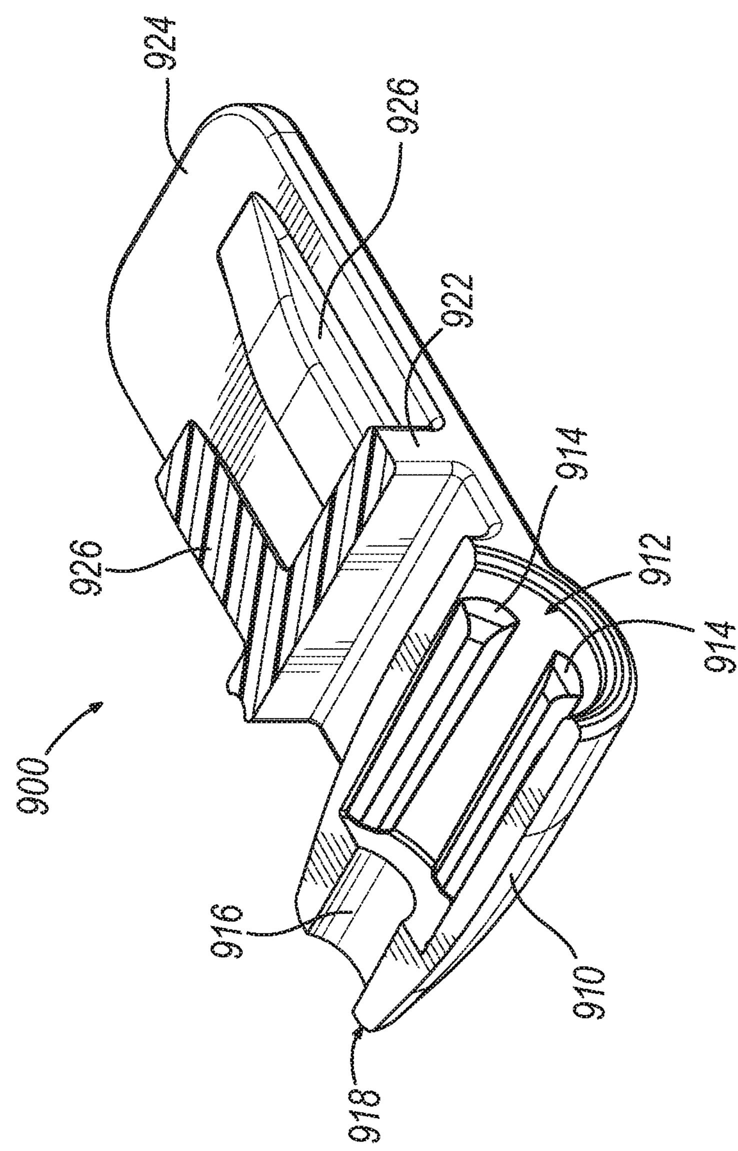
FIG. 11 depicts a perspective cross-sectional view of a sterile guide of the maker delivery device of FIG. 10, the cross-section taken along line 11-11 of FIG. 10.
Figure 12:
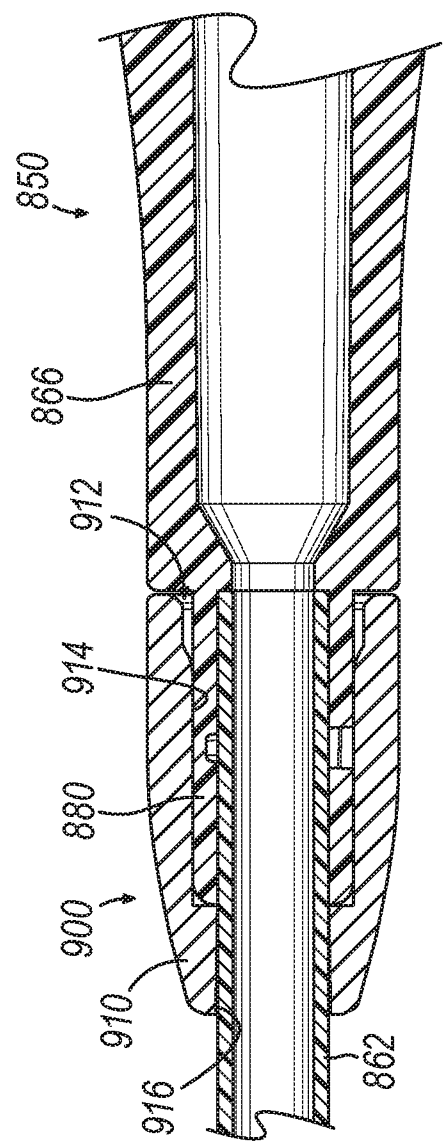
FIG. 12 depicts a side-cross-sectional view of the marker delivery device of FIG. 10.

FIGS. 10 through 12 depict a marker delivery device (850) that is substantially similar to marker delivery device (550) described above. For instance, like marker delivery device (550), marker delivery device (850) of the present example includes an elongate outer cannula (862) having a side opening or marker exit (864). Outer cannula (862) includes a distal tip (872) and is generally sized to slidably fit within a cutter or needle of biopsy device (700), as will be described in greater detail below. Similarly, the length of cannula (862) is generally sized to correspond to the length of a corresponding cutter or needle. It should be understood that in some examples the particular length of cannula (862) can be greater than the length of a cutter or needle. For instance, in some examples the proximal end of a cutter or needle can be coupled to a tissue sample holder or other tissue collection device. In such examples, the length of cannula (862) can have a length suitable to extend through both needle/cutter and various tissue collection devices.

Like with marker delivery device (550), marker delivery device (850) of the present example includes a grip (866) at the proximal end of cannula (862). Similarly, a push rod (868) can be provided, with push rod (868) extending coaxially in cannula (862) and extending proximally from grip (866). Like push rod (568) described above, push rod (868) of the present example is configured to translate within cannula (862) to displace one or more markers through side opening (864). Push rod (868) generally can have sufficient rigidity in compression to push a marker from an internal lumen (not shown) of cannula (862) out through opening (864), yet be relatively flexible in bending. A plunger (870) is coupled at the proximal end of push rod (868) for forcing push rod (868) distally in cannula (862) to deploy a marker out of cannula (862).

Like with grip (566) described above, an operator can grasp grip (866) with two fingers, and push on plunger (870) using the thumb on the same hand, so that marker delivery device (860) is operated by a single hand. A spring (not shown) or other resilient feature may be provided about push rod (868) to bias push rod (868) proximally relative to grip (866) and cannula (862).

As with marker delivery device (550) described above, marker delivery device (850) of the present example further includes a sterile guide (900). It should be understood that unless otherwise noted herein, sterile guide (900) of the present example is substantially similar to sterile guide (600) described above. As will be described in greater detail below, at least a portion of sterile guide (900) of the present example is generally configured to pivot and temporarily deform in shape to aid in detachment from grip (855).

As best seen in FIGS. 10 and 11, sterile guide (900) includes a body (910) with a grasping element or grip feature (920) extending therefrom. Body (910) is generally configured to receive cannula (862). In particular, body (910) defines a bore (912) extending through a central axis of body (910). Bore (912) is generally sized to receive cannula (862).

The interior of body (910) defined by bore (912) is shown in greater detail in FIG. 11. As can be seen, a proximal portion of body (910) includes a plurality of ribs (914) extending inwardly from the interior surface of body (910) defined by bore (912). Meanwhile, a distal portion of body (910) includes a cannula grip (916) extending inwardly relative to the interior surface of body (910). As will be described in greater detail below, ribs (914) are generally configured to engage at least a portion of grip (866) to provide an interference or friction fit between body (910) and grip (866). In the present example, three ribs (914) are shown on a single side of body (910). Although not shown, it should be understood that the upper side of body (910) includes a substantially similar configuration with respect to ribs (914). Thus, it should be understood that body (910) of the present example includes six ribs (914) with three ribs (914) arranged at equal distances on each side (e.g., upper and lower) of body (910). Although body (910) of the present example is shown as having a specific number of ribs (914), it should be understood that in other examples, any suitable number of ribs (914) can be used to provide a friction or interference fit between body (910) and grip (866).

Ribs (914) of the present example are integral with body (910). Accordingly, ribs (914) have generally substantially similar material properties as body (910). However, it should be understood that in other examples, ribs (914) can be configured as separate components attached to body (910). For instance, in some examples, ribs (914) can be configured as elastomeric portions attached to body (910) by adhesive bonding, mechanical bonding or any other suitable means.

Cannula grip (916) is generally configured to provide an interference or friction fit between body (910) and outer cannula (862). In particular, cannula grip (916) defines a semi-circular surface in bore (912) that generally corresponds to the outer diameter of outer cannula (862). In the present example, this semi-circular surface is slightly undersized relative to the outer diameter of outer cannula (862) to thereby provide an interference or friction fit. Although not show, it should be understood that cannula grip (916) having a substantially similar surface is included on the upper portion of body (910). Thus, it should be understood that the cannula grip (916) on each side of body (910) cooperates with the other to generally provide an interference or friction fit with outer cannula (862). As will be described in greater detail below, this configuration is generally configured to permit body (910) to have a selective locking function when used with outer cannula (862). In other words, body (910) is generally configured such that body (910) can be selectively positioned at a given axial position by an operator along the length of outer cannula (862) and then remain in such a position until changed by an operator.

Unlike sterile guide (600) described above, sterile guide (900) of the present example is generally configured to flex and/or deform to facilitate coupling and decoupling with grip (866). To permit such flexing and/or deformation, body (910) of the present example is generally slotted. As can be seen, body (910) is bisected by a pair of slots (918) oriented on opposing sides of body (910) and extending therethrough. Thus, as noted above, body (910) is separated into a lower and upper portion, yet each portion generally corresponds to the other. As will be described in greater detail below, slots (918) generally permit the upper portion of body (910) and lower portion of body (910) to pivot away from each other to selectively engage and disengage the interference or friction fit between body (910) and grip (866) and/or outer cannula (862).

As with sterile guide (600) described above, sterile guide (900) of the present example includes a grip feature (920). Like grip feature (620) described above, grip feature (920) of the present example is generally configured to promote gripping by an operator to move sterile guide (900) along the length of outer cannula (862). However, unlike grip feature (620) described above, grip feature (920) of the present example is generally configured to manipulate at least a portion of body (910) to actuate certain features of body (910) that will be described in greater detail below.

As best seen in FIG. 10, grip feature (920) includes a connector or connecting member (922) extending between a pair of arms (924). Connecting member (922) is generally positioned between arms (924) to act as a pivot for arms (924). As will be described in greater detail below, this configuration generally permits arms (924) to be squeezed together by an operator to pivot body (910) from a neutral closed configuration to an open configuration. In view of this configuration, it should be understood that the thickness, height, and relative position of connecting member (922) are all configured to promote pivoting of arms (924) and body (910). For instance, the thickness of connecting member (922) is generally thick enough to promote separation of arms (924), yet thin enough to provide some flexibility. Similarly, connecting member (922) is configured with a sufficient height to provide a setoff distance between arms (924) suitable to provide clearance for pivoting. Finally, the connecting member (922) is positioned relative to an outside end of each arm (924) to provide sufficient leverage for pivoting.

In some configurations, the various parameters of connecting member (922) can be at least partially determined by the material of connecting member (922). For instance, in the present example, sterile guide (900) is formed entirely of ABS plastic. As a result, the thickness, height, and relative position of connection member (922) can all be configured to reflect the specific hardness and elasticity of ABS plastic. In other examples, connection member (922) can comprise a different material relative to other portions of sterile guide (900). By way of example only, in some examples, connecting member (922) can be formed of an elastomer with greater flexibility relative to ABS plastic. In such examples, the particular configuration of connection member (922) can be adjusted to reflect such increased flexibility.

Arms (924) project outwardly from connection member (922). As noted above, arms (924) are generally configured to pivot about connecting member (922) to move body (910) from a neutral closed configuration to an open configuration. To facilitate this pivoting, arms (924) are generally configured with sufficient stiffness to avoid bending during pivoting. To promote stiffness, each arm (924) includes a strut (926) projecting inwardly from an interior surface of each arm (924). Each strut (926) is generally configured as an elongate rectangular projection. In addition, each strut (926) is offset relative to the other to prevent contact between struts (926) during pivoting of arms (924).

Sterile guide (900) is generally configured to couple to grip (866) of marker delivery device (850). In particular, as best seen in FIG. 10, marker delivery device (850) includes a retainer (880) extending distally from grip (866). Retainer (880) of the present example is generally cylindrical in shape and is configured to fit within bore (912) of sterile guide (900). However, unlike retainer (580) described above, retainer (880) of the present example omits a structure similar to rib (582). Instead, retainer (880) defines a relatively smooth surface.

As best seen in FIG. 12, sterile guide (900) is configured to fasten to retainer (880) of grip (866) by an interference or compression fit. In particular, FIG. 12 shows sterile guide (900) with body (910) in the neutral closed position referred to above. In this position, ribs (914) contact retainer (880) with some resiliency provided by connection member (922). This configuration provides sufficient friction between ribs (914) and retainer (880) to hold sterile guide (900) in position on grip (866). Similarly, the cannula grip (916) on each side of body (910) contacts outer cannula (862) with some resiliency provided by connection member (922). This configuration likewise provides sufficient friction between each cannula grip (916) and outer cannula (862) to hold sterile guide (900) in position on outer cannula (862).

Figure 13:
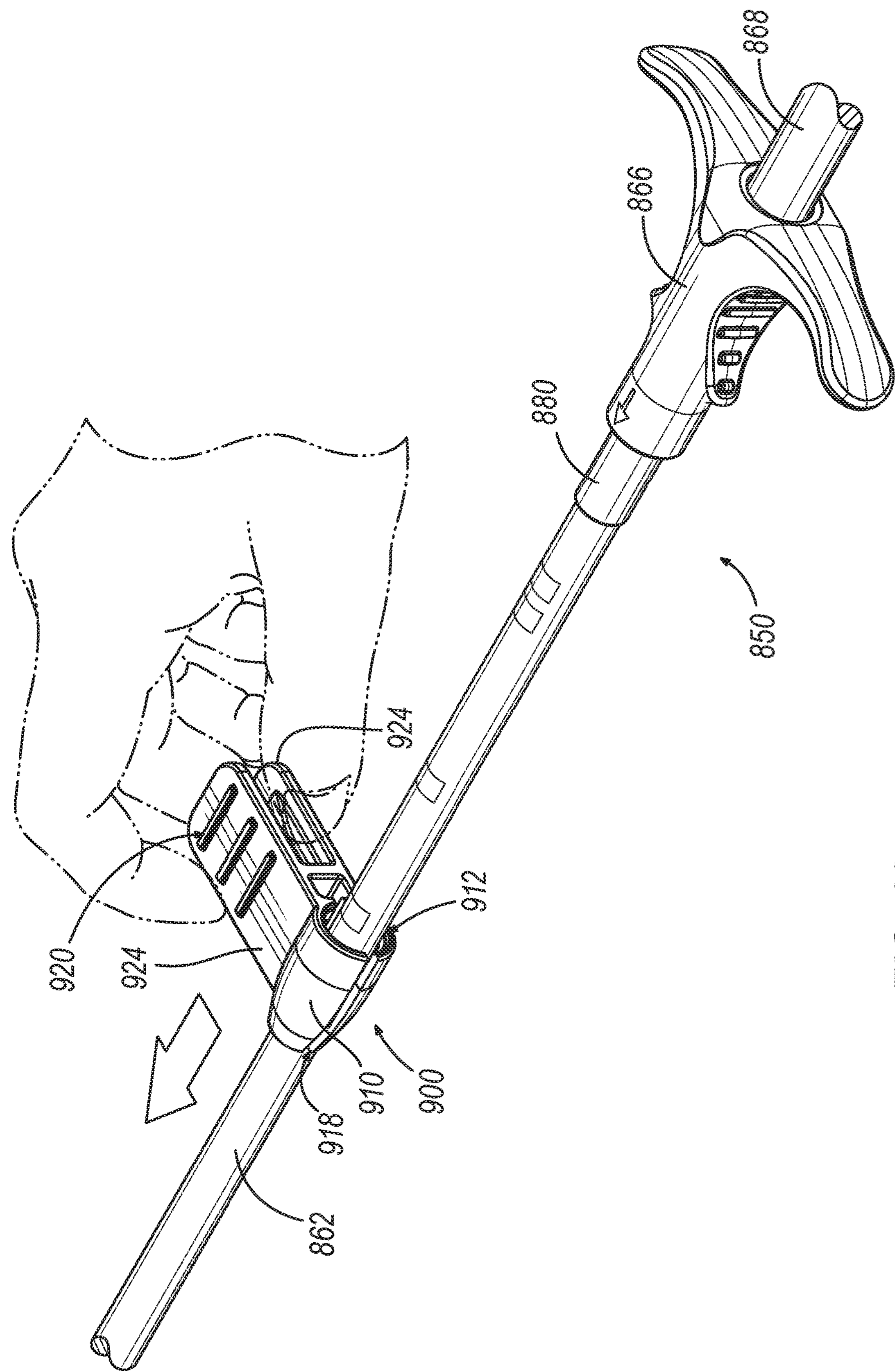
FIG. 13 depicts a detailed perspective view of the marker delivery device of FIG. 10, with the sterile guide being moved distally.
Figure 14:
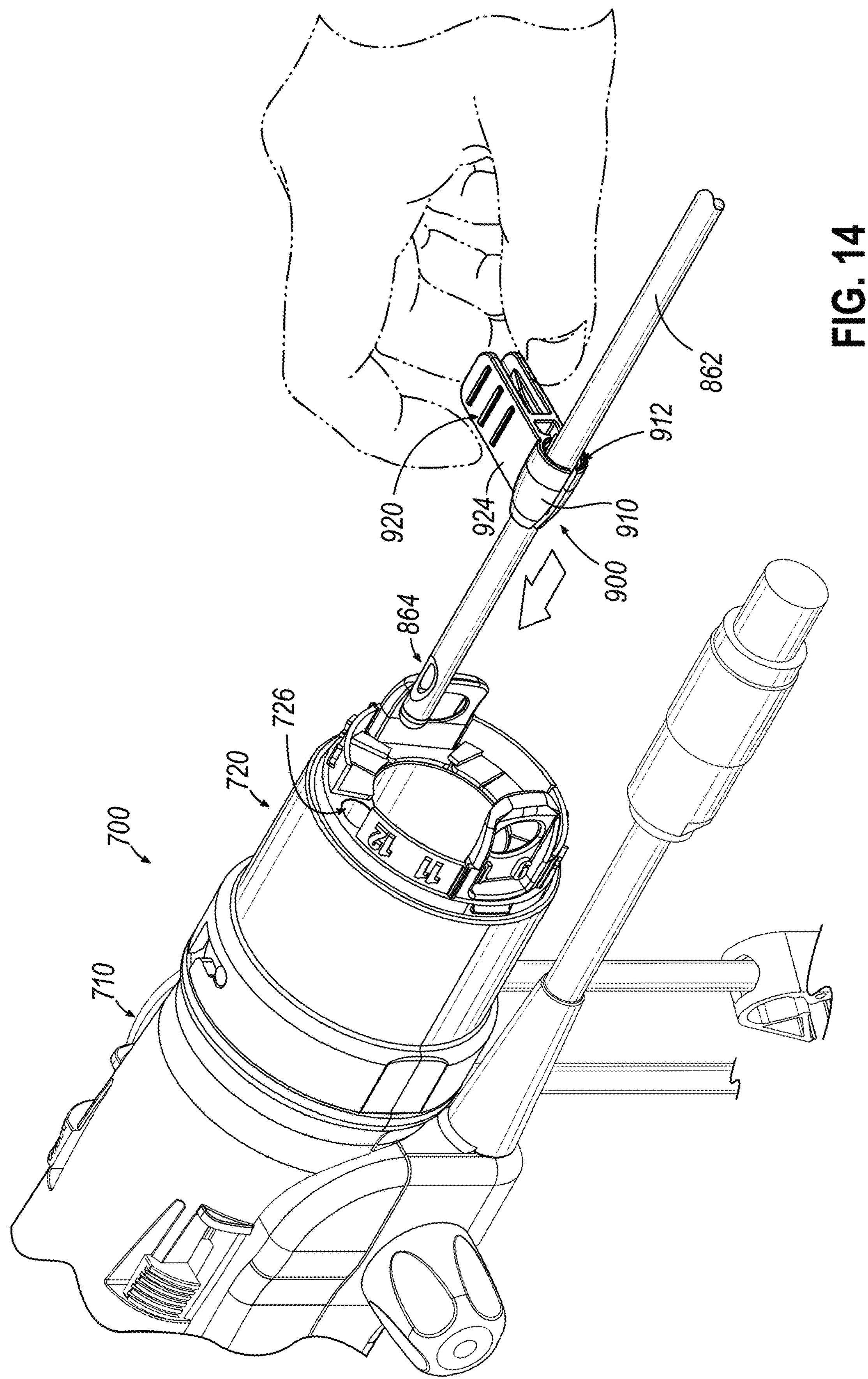
FIG. 14 depicts a detailed perspective view of the marker delivery device of FIG. 10 being inserted into the biopsy device of FIG. 9.

FIGS. 13 and 14 show an exemplary use of sterile guide (900). As can be seen in FIG. 13, sterile guide (900) is initially pulled distally from retainer (880) of marker delivery device (850). This pulling motion is combined with an operator squeezing arms (924) of sterile guide (900) together. Squeezing arms (924) generates a pivoting action at connection member (922), which drives the upper and lower portion of body (910) apart to expand slots (918). This effectively expands the diameter of bore (912) to reduce friction between ribs (914) and retainer (880), and between cannula grip (916) and outer cannula (862). Consequently, sterile guide (900) can be released from retainer (880) and can be freely slid axially down the length of outer cannula (862). At this stage, marker delivery device (850) can be pulled from associated packaging or otherwise be manipulated around a procedure room by gasping both grip (866) and sterile guide (900) using grip feature (920). Thus, sterile guide (900) can generally be placed towards distal tip (872) of outer cannula (862), but can be placed in any other suitable position along the length of outer cannula (862). At any desirable stage, the axial position of sterile guide (900) can be fixed along outer cannula (862) by releasing the pressure or squeezing applied to arms (924). This permits friction to increase between cannula grip (916) and outer cannula (862). However, it should be understood that arms (924) can still be used to manipulate outer cannula (862) while sterile guide (900) remains locked in position.

Once sterile guide (900) is positioned as desired, an operator can use sterile guide (900) to manipulate outer cannula (862) into a biopsy device, biopsy needle, targeting set, introducer, or other components associated with a patient. One merely exemplary example of manipulation is show in FIG. 14. As can be seen, sterile guide (900) is used to manipulate distal tip (872) of outer cannula (862) into marking port (726) of tissue sample holder (720) that is attached to a proximal end of biopsy probe (710) of biopsy device (700). In particular, an operator can grasp grip feature (920) to manipulate outer cannula (862) without physically touching outer cannula (862). Due to the positioning of sterile guide (900) proximate the distal end of outer cannula (862), movement of distal tip (872) is easily controlled to position distal tip (872) into port (726). It should be understood that in some examples, biopsy device (700) can be constructed in accordance with at least some of the teachings of U.S. Pat. No. 9,877,706, entitled "Biopsy Device," issued on Jan. 30, 2018, the disclosure of which is incorporated by reference herein.

Although not shown, it should be understood that tissue sample holder (720) of the present example is rotatable to align port (726) with a cutter of biopsy device (700). The cutter is disposed within a needle similar to needle (400) described above that extends distally from probe (710). Thus, the cutter can act as a conduit between port (726) and the needle so that outer cannula (862) can be used to deploy marker (100) through side opening (864). Although marker delivery device (850) and sterile guide (900) of the present example are shown as being used in connection with biopsy device (700), it should be understood that in other examples the combination of marker delivery device (850) and sterile guide (900) can be used with a variety of other biopsy devices or other medical instruments. For instance, in some examples, outer cannula (862) can be inserted directly into a cutter under the direction of sterile guide (900). In other examples, outer cannula (862) can be inserted using sterile guide (900) through a basket-style tissue sample holder constructed in accordance with the teachings of U.S. Pat. No. 9,999,406, the disclosure of which is incorporated by reference herein. In still other examples, outer cannula (862) can be inserted using sterile guide (900) through an introducer constructed in accordance with the teachings of U.S. Pat. No. 9,788,819, the disclosure of which is incorporated by reference herein. In yet other examples, the combination of marker delivery device (850) and sterile guide (900) can be used with various alternative devices as will be apparent to those of ordinary skill in the art in view of the teachings herein.

Once outer cannula (862) is inserted into port (726) or any other suitable component, sterile guide (900) can be slid proximally along outer cannula (862) back to retainer (880). Sterile guide (900) can then be re-coupled to retainer (880) for storage while marking is performed. In other examples, sterile guide (900) can be removed entirely from outer cannula (862) by squeezing arms (924) to a point sufficient to expand slots (918) to a size greater than the outer diameter of outer cannula (862). Sterile guide (900) can then be removed by pulling arms (924) transversely relative to outer cannula (862). Regardless, after marking, sterile guide (900) can then be again de-coupled from retainer (880), or otherwise reattached to outer cannula (862), to provide assistance to an operator with removal of outer cannula (862) from port (726) or any other suitable component. After the procedure is complete, marker delivery device (850) and sterile guide (900) can together be disposed of.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus for delivery biopsy markers to a biopsy site, the apparatus comprising: a grip, a cannula extending distally from the grip and having a lumen extending at least partially therethrough, and a maker exit opening communicating with the lumen; at least one biopsy marker disposed in the lumen for deployment through the marker exit opening in the cannula; and a sterile guide slidable along the cannula and configured to fasten to the grip.

EXAMPLE 2

The apparatus of Example 1, wherein the sterile guide is positionable along the length of the cannula between the grip and a distal tip of the cannula.

EXAMPLE 3

The apparatus of any one or more of Examples 1 through 2, further comprising a retainer extending from the grip, wherein the retainer is configured to couple the sterile guide to the grip.

EXAMPLE 4

The apparatus of Example 3, wherein the retainer is configured to provide tactile feedback when the sterile guide is coupled to the retainer.

EXAMPLE 5

The apparatus of any one or more of Examples 3 or 4, wherein the retainer is configured to provide an audible noise when the sterile guide is coupled to the retainer.

EXAMPLE 6

The apparatus of any one or more of Examples 1 through 5, wherein the sterile guide includes a body associated with the cannula and a grasping element protruding outwardly from a side of the body.

EXAMPLE 7

The apparatus of Example 6, wherein the body defines a bore, wherein the bore has an inner diameter corresponding to the outer diameter of the cannula.

EXAMPLE 8

The apparatus of Example 7, wherein the inner diameter of the bore is sized to have an interference fit with the outer diameter of the cannula such that the body is movable relative to the cannula with application of a force.

EXAMPLE 9

The apparatus of Example 7, wherein the body is formed of an elastomer material such that the body is configured to remain in a selected position relative to the cannula but slide along the length of the cannula when a force is applied by an operator.

EXAMPLE 10

A biopsy system comprising: a biopsy device operable for taking one or more biopsy samples from a patient, the biopsy device comprising a needle and a cutter for severing tissue received within the needle; a marker delivery device, the marker delivery device including a handle and a cannula extending distally from the handle having a marker lumen and at least one marker disposed in the marker lumen, and a movable member positionable on the cannula, wherein the movable member is removably coupled to the handle and is configured to slide along the length of the cannula when de-coupled from the handle to direct the cannula into the needle of the biopsy device.

EXAMPLE 11

The biopsy system of Example 10, wherein the movable member is positionable on the cannula to a position proximate a distal tip of the cannula to define a desired insertion portion of the cannula into the needle of the biopsy device.

EXAMPLE 12

The biopsy system of any one or more of Examples 10 and 11, wherein the movable member includes a grip feature configured for gasping by an operator to manipulate the movable member.

EXAMPLE 13

The biopsy system of any one or more of Examples 10 through 12, wherein the movable member includes a body having a coupling feature, wherein the coupling feature is configured to engage a retainer associated with the handle.

EXAMPLE 14

The biopsy system of Examples 13, wherein the coupling feature includes a counterbore face and an inwardly oriented protrusion, wherein the counterbore face and the protrusion are configured to engage a rib of the retainer to couple the movable member to the retainer.

EXAMPLE 15

The biopsy system of Example 14, wherein the movable member is configured to slide axially along the length of the cannula when de-coupled from the retainer for manipulation of the cannula while maintaining sterility of the cannula.

EXAMPLE 16

An apparatus for delivery biopsy markers to a biopsy site, the apparatus comprising: a grip, a cannula extending distally from the grip and having a lumen extending at least partially therethrough, and a maker exit opening communicating with the lumen; at least one biopsy marker disposed in the lumen for deployment through the marker exit opening in the cannula; and a sterile guide slidable along the cannula and configured to selectively fasten to the grip and the cannula simultaneously.

EXAMPLE 17

The apparatus of Example 16, wherein the sterile guide includes a body defining a bore and one or more arms projecting laterally from the body, wherein the bore is configured to receive the cannula therethrough, wherein the body is configured to selectively expand a diameter of the bore to permit selective fastening of the body to the grip.

EXAMPLE 18

The apparatus of Example 16, wherein the sterile guide includes a body defining a bore and one or more arms projecting laterally from the body, wherein the bore is configured to receive the cannula and at least a portion of the grip, wherein the body is configured to selectively transition between a closed configuration and an open configuration, wherein the body is configured to fasten to the grip when in the closed configuration, wherein the body is configured to slide along the cannula when in the open configuration.

EXAMPLE 19

The apparatus of Example 16, wherein the sterile guide includes a body defining a bore and one or more arms projecting laterally from the body, wherein the bore is configured to receive the cannula and at least a portion of the grip, wherein the body is configured to selectively transition between a closed configuration and an open configuration, wherein the body is configured to fasten to the grip when in the closed configuration, wherein the body is configured to slide along the cannula when in the open configuration, wherein at least a portion of the sterile guide is configured to resiliently bias the body towards the closed configuration.

EXAMPLE 20

The apparatus of Example 16, wherein the sterile guide includes a body defining a bore, a pair of arms projecting laterally from the body, and a connection member extending between each arm of the pair of arms, wherein the bore is configured to receive the cannula therethrough, wherein each arm of the pair of arms is configured to pivot about the connection member to move the body and thereby permit selective fastening of the body to the grip.

EXAMPLE 21

The apparatus of Example 16, wherein the sterile guide includes a body defining a bore, a pair of arms projecting laterally from the body, and a connection member extending between each arm of the pair of arms, wherein the bore is configured to receive the cannula therethrough, wherein each arm of the pair of arms is configured to pivot about the connection member to move the body between a closed configuration and an open configuration, wherein the body is configured to selectively fasten to the grip when in the closed configuration, wherein the body is configured to slide along the cannula when in the open configuration.

EXAMPLE 22

The apparatus of Example 16, wherein the sterile guide includes a body defining a bore, a pair of arms projecting laterally from the body, and a connection member extending between each arm of the pair of arms, wherein the bore is configured to receive the cannula therethrough, wherein each arm of the pair of arms is configured to pivot about the connection member to move the body between a closed configuration and an open configuration, wherein the body is configured to selectively fasten to the grip when in the closed configuration, wherein the body is configured to slide along the cannula when in the open configuration, wherein the connection member is configured to resiliently bias the body towards the closed configuration.

EXAMPLE 23

The apparatus of Example 16, wherein the grip includes a retainer, wherein the sterile guide includes a body defining a bore, a pair of arms projecting laterally from the body, and a connection member extending between each arm of the pair of arms, wherein the body includes a cannula grip and a plurality of ribs projecting into the interior of the bore, wherein each arm of the pair of arms is configured to pivot about the connection member to move the body between a closed configuration and an open configuration, wherein the body is configured to provide an interference fit between the ribs and the retainer when in the closed configuration, wherein the body is configured to further provide an interference fit between the cannula grip and the cannula when in the closed configuration, wherein the body is configured to slide along the cannula when in the open configuration.

EXAMPLE 24

The apparatus of Example 16, wherein the grip includes a retainer, wherein the sterile guide includes a body defining a bore, a pair of arms projecting laterally from the body, and a connection member extending between each arm of the pair of arms, wherein the body includes a cannula grip and a plurality of ribs projecting into the interior of the bore, wherein each arm of the pair of arms is configured to pivot about the connection member to move the body between a closed configuration and an open configuration, wherein the body is configured to provide a friction fit between the ribs and the retainer when in the closed configuration, wherein the body is configured to further provide an friction fit between the cannula grip and the cannula when in the closed configuration, wherein the body is configured to slide along the cannula when in the open configuration, wherein the connection member is configured to resiliently bias the body towards the closed position to thereby provide friction between the ribs and the retainer, and the cannula grip and the cannula.

EXAMPLE 25

The apparatus of Example 16, wherein the sterile guide includes a body defining a bore and one or more arms projecting laterally from the body, wherein the bore is configured to receive the cannula therethrough, wherein the body is configured to selectively fasten to the grip by a friction fit between a portion of the body and both a portion of the cannula and a portion of the grip.

EXAMPLE 26

The apparatus of Example 16, wherein the sterile guide includes a body defining a bore and one or more arms projecting laterally from the body, wherein the body includes a plurality of ribs and a cannula grip projecting into the bore, wherein the body is configured to selectively fasten to the grip by a friction fit between the plurality of ribs and a portion of the grip, and a friction fit between the cannula grip and the cannula.

EXAMPLE 27

The apparatus of any one or more of Examples 16 through 22 and 25 through 26, further comprising a retainer extending from the grip, wherein the retainer is configured to couple the sterile guide to the grip.

EXAMPLE 28

The apparatus of Example 27, wherein the retainer is configured to provide tactile feedback when the sterile guide is coupled to the retainer.

EXAMPLE 29

The apparatus of any one or more of Examples 27 or 28, wherein the retainer is configured to provide an audible noise when the sterile guide is coupled to the retainer.

EXAMPLE 30

The apparatus of any one or more of Examples 27 through 29, wherein the retainer includes a detent feature, wherein the sterile guide includes a corresponding detent feature configured to engage the detent feature of the retainer.

EXAMPLE 31

A biopsy system comprising: a biopsy device operable for taking one or more biopsy samples from a patient, the biopsy device comprising a needle and a cutter for severing tissue received within the needle; a marker delivery device, the marker delivery device including a handle and a cannula extending distally from the handle having a marker lumen and at least one marker disposed in the marker lumen, and a sterile guide positionable on the cannula, wherein the sterile guide is removably coupled to the handle and the cannula, simultaneously, and is configured to selectively slide along the length of the cannula when de-coupled from the handle to direct the cannula into the needle of the biopsy device.

EXAMPLE 32

The biopsy system of Example 31, wherein the sterile guide is positionable along an axial length of the cannula, wherein the sterile guide is configured to selectively lock into any one of a plurality of positions along the axial length of the cannula.

EXAMPLE 33

The biopsy system of any one or more of Examples 31 or 32, wherein the sterile guide includes a body, a pivot, and a grip feature extending from the pivot, wherein the pivot is configured to resiliently bias the body towards a closed position to provide a friction fit between any one or more of the body and the handle, or the body and the cannula.

EXAMPLE 34

The system of Example 33, wherein the body includes a coupling feature, wherein the handle includes a retainer, wherein the coupling feature is configured to engage the retainer to couple the sterile guide to the handle.

EXAMPLE 35

A method for guiding a marker delivery device relative to a biopsy instrument, the method comprising: preparing the marker delivery device for removal from a package by detaching a sterile guide from a handle of the marker delivery device and sliding the sterile guide along a cannula of the marker delivery device to a deployment position proximate a distal tip of the cannula; removing the marker delivery device from the package by grasping the sterile guide and the handle of the marker delivery device; and guiding the distal tip of the cannula into a portion of the biopsy instrument by aligning the sterile guide with the biopsy instrument.

EXAMPLE 36

The method of Example 35, wherein the step of preparing the marker delivery device includes expanding the internal diameter of a body of the sterile guide to detach the sterile guide from the handle of the marker delivery device.

EXAMPLE 37

The method of Example 35, wherein the step of preparing the marker delivery device includes squeezing at least one arm extending from a body of the sterile guide to expand the internal diameter of the body to detach the sterile guide from the handle of the marker delivery device.

EXAMPLE 38

The method of any one or more of Examples 35 through 37, wherein the step of preparing the marker delivery device includes pulling the sterile guide axially away from the handle of the marker delivery device to release a detent feature from a corresponding detent feature associated with the handle of the marker delivery device.

EXAMPLE 39

An apparatus for delivery of a biopsy marker to a biopsy site, the apparatus comprising: a grip and a cannula extending distally from the grip, the cannula having a lumen extending at least partially therethrough and a marker exit opening in the cannula communicating with the lumen; at least one biopsy marker disposed in the lumen for deployment through the marker exit opening; and a sterile guide including a body configured to slide along the cannula, wherein the sterile guide further includes a radially extending grasping feature of unitary construction with the body.

EXAMPLE 40

The apparatus of Example 39, wherein the body defines a bore, wherein the grasping feature includes one or more arms projecting laterally from the body, wherein the bore is configured to receive the cannula and at least a portion of the grip, wherein the body is configured to selectively transition between a closed configuration and an open configuration, wherein the body is configured to fasten to the grip when in the closed configuration, wherein the body is configured to slide along the cannula when in the open configuration, wherein at least a portion of the sterile guide is configured to resiliently bias the body towards the closed configuration.

EXAMPLE 41

The apparatus of Example 39, wherein the body defines a bore, wherein the grasping feature includes a pair of arms projecting laterally from the body, wherein the sterile guide further includes a connection member extending between each arm of the pair of arms, wherein the bore is configured to receive the cannula therethrough, wherein each arm of the pair of arms is configured to pivot about the connection member to move the body and thereby permit selective fastening of the body to the grip.

EXAMPLE 42

The apparatus of Example 39, wherein the body defines a bore, wherein the grasping feature includes a pair of arms projecting laterally from the body, wherein the sterile guide further includes a connection member extending between each arm of the pair of arms, wherein the bore is configured to receive the cannula therethrough, wherein each arm of the pair of arms is configured to pivot about the connection member to move the body between a closed configuration and an open configuration, wherein the body is configured to selectively fasten to the grip when in the closed configuration, wherein the body is configured to slide along the cannula when in the open configuration.

EXAMPLE 43

The apparatus of Example 39, wherein the body defines a bore, wherein the grasping feature includes a pair of arms projecting laterally from the body, wherein the sterile guide further includes a connection member extending between each arm of the pair of arms, wherein the bore is configured to receive the cannula therethrough, wherein each arm of the pair of arms is configured to pivot about the connection member to move the body between a closed configuration and an open configuration, wherein the body is configured to selectively fasten to the grip when in the closed configuration, wherein the body is configured to slide along the cannula when in the open configuration, wherein the connection member is configured to resiliently bias the body towards the closed configuration.

EXAMPLE 44

The apparatus of claim 39, wherein the grip includes a retainer, wherein the body defines a bore, wherein the grasping feature includes a pair of arms projecting laterally from the body, wherein the sterile guide further includes a connection member extending between each arm of the pair of arms, wherein the body includes a cannula grip and a plurality of ribs projecting into the interior of the bore, wherein each arm of the pair of arms is configured to pivot about the connection member to move the body between a closed configuration and an open configuration, wherein the body is configured to provide a friction fit between the ribs and the retainer when in the closed configuration, wherein the body is configured to further provide an friction fit between the cannula grip and the cannula when in the closed configuration, wherein the body is configured to slide along the cannula when in the open configuration, wherein the connection member is configured to resiliently bias the body towards the closed position to thereby provide friction between the ribs and the retainer, and the cannula grip and the cannula.

EXAMPLE 45

The apparatus of Example 39, wherein the body defines a bore, wherein the grasping feature includes one or more arms projecting laterally from the body, wherein the body includes a plurality of ribs and a cannula grip projecting into the bore, wherein the body is configured to selectively fasten to the grip by a friction fit between the plurality of ribs and a portion of the grip, and a friction fit between the cannula grip and the cannula.

EXAMPLE 46

The apparatus of any one or more of Examples 39 through 45, further comprising a retainer extending from the grip, wherein the retainer is configured to couple the sterile guide to the grip.

EXAMPLE 47

The apparatus of Example 46, wherein the retainer is configured to provide tactile feedback when the sterile guide is coupled to the retainer.

EXAMPLE 48

The apparatus of Example 46, wherein the retainer includes a detent feature, wherein the sterile guide includes a corresponding detent feature configured to engage the detent feature of the retainer.

V. Conclusion

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for delivery of a biopsy marker to a biopsy site, the apparatus comprising:

(a) a grip and a cannula extending distally from the grip, the cannula having a lumen extending at least partially therethrough and a marker exit opening in the cannula communicating with the lumen;

(b) at least one biopsy marker disposed in the lumen for deployment through the marker exit opening; and (c) a sterile guide including a body configured to slide along the cannula, the body defining a bore, the sterile guide further including a radially extending grasping feature of unitary construction with the body, the grasping feature including a pair of arms projecting laterally from the body and a connection member disposed between the pair of arms and offset from the body, the bore being configured to receive the cannula and at least a portion of the grip, the body being configured to transition between a closed configuration and an open configuration in response to movement of the pair of arms towards each other and relative to the connection member, the body being configured to fasten to the grip when in the closed configuration, the body being configured to slide along the cannula in the open configuration, and the body including a plurality of ribs and a cannula grip projecting into the bore from opposite sides of the body, each rib extending perpendicularly from a transverse surface defined by a portion of the cannula grip, the body being configured to selectively fasten to the grip by a friction fit between the plurality of ribs and a portion of the grip, and a friction fit between the cannula grip and the cannula.

2. The apparatus of claim 1, the body being configured to selectively expand a diameter of the bore to permit selective fastening of the body to the grip.

3. The apparatus of claim 1, at least a portion of the sterile guide being configured to resiliently bias the body towards the closed configuration.

4. The apparatus of claim 1, each arm of the pair of arms being configured to pivot about the connection member to move the body and thereby permit selective fastening of the body to the grip.

5. The apparatus of claim 1, each arm of the pair of arms being configured to pivot about the connection member to move the body between the closed configuration and the open configuration.

6. The apparatus of claim 1, each arm of the pair of arms being configured to pivot about the connection member to move the body between the closed configuration and the open configuration, the connection member being configured to resiliently bias the body towards the closed configuration.

7. The apparatus of claim 1, the grip including a retainer, each arm of the pair of arms being configured to pivot about the connection member to move the body between the closed configuration and the open configuration, the body being configured to provide an interference fit between the ribs and the retainer when in the closed configuration, the body being configured to further provide an interference fit between the cannula grip and the cannula when in the closed configuration.

8. The apparatus of claim 1, the grip including a retainer, each arm of the pair of arms being configured to pivot about the connection member to move the body between the closed configuration and the open configuration, the body being configured to provide a friction fit between the ribs and the retainer when in the closed configuration, the connection member being configured to resiliently bias the body towards the closed position to thereby provide friction between the ribs and the retainer, and the cannula grip and the cannula.

9. The apparatus of claim 1, further comprising a retainer extending from the grip, the retainer being configured to couple the sterile guide to the grip.

10. The apparatus of claim 9, the retainer being configured to provide tactile feedback when the sterile guide is coupled to the retainer.

11. The apparatus of claim 9, the retainer being configured to provide an audible noise when the sterile guide is coupled to the retainer.

12. The apparatus of claim 9, the retainer including a detent feature, the sterile guide including a corresponding detent feature configured to engage the detent feature of the retainer.

13. A biopsy system comprising:

(a) a biopsy device operable for taking one or more biopsy samples from a patient, the biopsy device comprising a needle and a cutter for severing tissue received within the needle;

(b) a marker delivery device, the marker delivery device including a handle and a cannula extending distally from the handle having a marker lumen and at least one marker disposed in the marker lumen; and (c) a sterile guide positionable on the cannula, the sterile guide being removably coupled to the handle and the cannula, simultaneously, and being configured to selectively slide along the length of the cannula when de-coupled from the handle to direct the cannula into the needle of the biopsy device, the sterile guide including a body, a pivot, and a grip feature extending from the pivot, the body including a cannula grip and a plurality of ribs, the cannula grip extending through a first axial portion of the body, the cannula grip defining a gripping surface and a proximal surface, the proximal surface oriented transversely relative to the gripping surface, each rib of the plurality of ribs projecting from the proximal surface of the cannula grip and extending axially through a second axial portion of the body, the pivot being offset relative to the body and configured to resiliently bias the body towards a closed position to provide a friction fit between any one or more of the ribs of the body and the handle, or the cannula grip of the body and the cannula.

14. The biopsy system of claim 13, the sterile guide being positionable along an axial length of the cannula, the sterile guide being configured to selectively lock into any one of a plurality of positions along the axial length of the cannula using the cannula grip.

15. The biopsy system of claim 13, the body including a coupling feature, the handle including a retainer, the coupling feature being configured to engage the retainer to couple the sterile guide to the handle.

16. A method for guiding a marker delivery device relative to a biopsy instrument, the method comprising:

(a) providing the marker delivery device disposed within a package, the marker delivery device including a sterile guide pre-attached to a handle of the marker delivery device before disposition of the marker delivery device within the package, a ribbed portion of the sterile guide being pre-attached to the handle, one or more ribs of the ribbed portion extending axially relative to the handle;

(b) preparing the marker delivery device for removal from the package by detaching the sterile guide from the handle of the marker delivery device and sliding the sterile guide along a cannula of the marker delivery device to a deployment position proximate a distal tip of the cannula;

(c) removing the marker delivery device from the package by grasping the sterile guide and the handle of the marker delivery device;

(d) engaging a smooth portion of the sterile guide with a portion of the cannula while the ribbed portion is disengaged from both the handle and the cannula to secure the sterile guide in a fixed position along the length of the cannula, the smooth portion extending inwardly relative to the ribbed portion; and (e) guiding the distal tip of the cannula into a portion of the biopsy instrument by aligning the sterile guide with the biopsy instrument.

* * * * *